US007588550B2

United States Patent
Leonard et al.

(10) Patent No.: US 7,588,550 B2
(45) Date of Patent: Sep. 15, 2009

(54) SYSTEMS AND METHODS OF BLOOD-BASED THERAPIES HAVING A MICROFLUIDIC MEMBRANELESS EXCHANGE DEVICE

(75) Inventors: Edward F. Leonard, Scarsdale, NY (US); Alan C. West, Tenafly, NJ (US); Nina C. Shaplely, New York, NY (US); Zhongliang Tang, San Diego, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/776,360

(22) Filed: Jul. 11, 2007

(65) Prior Publication Data

US 2008/0009780 A1    Jan. 10, 2008

Related U.S. Application Data

(62) Division of application No. 10/801,366, filed on Mar. 15, 2004, now abandoned.

(60) Provisional application No. 60/454,579, filed on Mar. 14, 2003.

(51) Int. Cl.
*A61M 37/00* (2006.01)
*B32B 27/04* (2006.01)
*B32B 27/12* (2006.01)

(52) U.S. Cl. .................... 604/5.04; 604/4.01; 604/5.01; 604/6.11; 604/6.16; 422/44

(58) Field of Classification Search .................. 210/97, 210/137, 200, 203, 209, 511, 634, 645, 646, 210/647, 767, 806; 604/5.01, 5.04, 6.01, 604/6.02, 6.09, 6.11; 422/81, 82, 99, 101; 209/155, 156
See application file for complete search history.

(56) References Cited

U.S. PATENT DOCUMENTS 2,885,782 A    5/1959    Groves (Continued)

FOREIGN PATENT DOCUMENTS

DE    20113789    5/2002

(Continued)

OTHER PUBLICATIONS

Co-pending U.S. Appl. No. 11/814,117 to Leonard.*

(Continued)

*Primary Examiner*—Leslie Deak
*Assistant Examiner*—Adam Marcetich
(74) *Attorney, Agent, or Firm*—Miles & Stockbridge P.C.; Mark A. Catan

(57) ABSTRACT

The present invention is directed to devices, systems and methods for removing undesirable materials from a sample fluid by contact with a second fluid. The sample fluid flows as a thin layer adjacent to, or between, concurrently flowing layers of the second fluid, without an intervening membrane. In various embodiments, a secondary separator is used to restrict the removal of desirable substances and effect the removal of undesirable substances from blood. The invention is useful in a variety of situations where a sample fluid is to be purified via a diffusion mechanism against an extractor fluid. Moreover, the invention may be used for the removal of components from a sample fluid that vary in size. When blood is the sample fluid, for example, this may include the removal of 'small' molecules, 'middle' molecules, macromolecules, macromolecular aggregates, and cells, from the blood sample to the extractor fluid.

26 Claims, 9 Drawing Sheets

U.S. PATENT DOCUMENTS

| | | |
|---|---|---|
| 3,388,803 A | 6/1968 | Scott |
| 3,506,126 A * | 4/1970 | Lindsay, Jr. et al. ......... 210/96.2 |
| 3,619,423 A * | 11/1971 | Galletti et al. .............. 210/632 |
| 3,746,175 A | 7/1973 | Markley |
| 3,799,873 A | 3/1974 | Brown ....................... 210/641 |
| 3,884,808 A | 5/1975 | Scott |
| 3,939,069 A | 2/1976 | Granger et al. .............. 210/637 |
| 3,989,622 A | 11/1976 | Marantz et al. |
| 3,994,799 A | 11/1976 | Yao et al. |
| 4,066,549 A | 1/1978 | Oeser et al. |
| 4,083,786 A * | 4/1978 | Tsuda et al. ........... 210/321.61 |
| 4,094,775 A | 6/1978 | Mueller ....................... 21/646 |
| 4,137,921 A | 2/1979 | Okuzumi et al. |
| 4,166,800 A | 9/1979 | Fong |
| 4,181,983 A | 1/1980 | Kulkarni |
| 4,212,738 A | 7/1980 | Henne |
| 4,212,742 A | 7/1980 | Solomon et al. |
| 4,243,775 A | 1/1981 | Rosensaft et al. |
| 4,247,393 A | 1/1981 | Wallace |
| 4,267,040 A | 5/1981 | Schal |
| 4,269,708 A | 5/1981 | Bonomini et al. |
| 4,279,249 A | 7/1981 | Vert et al. |
| 4,300,565 A | 11/1981 | Rosensaft et al. |
| 4,321,192 A * | 3/1982 | Jain ........................... 530/420 |
| 4,347,234 A | 8/1982 | Wahlig et al. |
| 4,384,975 A | 5/1983 | Fong |
| 4,390,519 A | 6/1983 | Sawyer |
| 4,394,370 A | 7/1983 | Jefferies |
| 4,409,332 A | 10/1983 | Jefferies et al. |
| 4,431,019 A | 2/1984 | Kopp et al. |
| 4,443,333 A | 4/1984 | Mahurkar |
| 4,530,449 A | 7/1985 | Nozawa et al. |
| 4,538,603 A | 9/1985 | Pawelchak et al. |
| 4,539,981 A | 9/1985 | Tunc |
| 4,563,489 A | 1/1986 | Urist |
| 4,568,559 A | 2/1986 | Nuwayser et al. |
| 4,578,384 A | 3/1986 | Hollinger |
| 4,585,797 A | 4/1986 | Cioca |
| 4,596,574 A | 6/1986 | Urist |
| 4,623,588 A | 11/1986 | Nuwayser et al. |
| 4,661,246 A | 4/1987 | Ash ............................. 210/87 |
| 4,663,049 A * | 5/1987 | Kolff et al. .................. 210/641 |
| 4,678,566 A * | 7/1987 | Watanabe et al. ........... 210/143 |
| 4,703,108 A | 10/1987 | Silver et al. |
| 4,741,337 A | 5/1988 | Smith et al. |
| 4,744,365 A | 5/1988 | Kaplan et al. |
| 4,765,899 A | 8/1988 | Wells et al. |
| 4,765,907 A * | 8/1988 | Scott ........................... 210/648 |
| 4,795,804 A | 1/1989 | Urist |
| 4,818,542 A | 4/1989 | DeLuca et al. |
| 4,822,278 A | 4/1989 | Oliva et al. |
| 4,837,285 A | 6/1989 | Berg et al. |
| 4,839,130 A | 6/1989 | Kaplan et al. |
| 4,844,854 A | 7/1989 | Kaplan et al. |
| 4,849,340 A | 7/1989 | Oberhardt |
| 4,877,864 A | 10/1989 | Wang et al. |
| 4,889,119 A | 12/1989 | Jamiolkowski et al. |
| 4,897,189 A | 1/1990 | Greenwood et al. |
| 4,898,186 A | 2/1990 | Ikada et al. |
| 4,898,734 A | 2/1990 | Mathiowitz et al. |
| 4,916,193 A | 4/1990 | Tang et al. |
| 4,938,763 A | 7/1990 | Dunn et al. |
| 4,961,707 A | 10/1990 | Magnusson et al. |
| 4,968,422 A | 11/1990 | Runge et al. |
| 4,968,590 A | 11/1990 | Kuberasampath et al. |
| 4,975,527 A | 12/1990 | Koezuka et al. |
| 4,997,570 A | 3/1991 | Polaschegg |
| 5,004,602 A | 4/1991 | Hutchinson |
| 5,007,939 A | 4/1991 | Delcommune et al. |
| 5,011,691 A | 4/1991 | Oppermann et al. |
| 5,011,692 A | 4/1991 | Fujioka et al. |
| 5,013,649 A | 5/1991 | Wang et al. |
| 5,037,639 A | 8/1991 | Tung |
| 5,051,272 A | 9/1991 | Hermes et al. |
| 5,077,049 A | 12/1991 | Dunn et al. |
| 5,080,665 A | 1/1992 | Jarrett et al. |
| 5,081,106 A | 1/1992 | Bentley et al. |
| 5,084,051 A | 1/1992 | Tormala et al. |
| 5,106,748 A | 4/1992 | Wozney et al. |
| 5,108,753 A | 4/1992 | Kuberasampath et al. |
| 5,108,755 A | 4/1992 | Daniels et al. |
| 5,116,738 A | 5/1992 | Wang et al. |
| 5,128,136 A | 7/1992 | Bentley et al. |
| 5,133,755 A | 7/1992 | Brekke |
| 5,141,905 A | 8/1992 | Rosen et al. |
| 5,143,730 A | 9/1992 | Fues et al. |
| 5,149,691 A | 9/1992 | Rutherford |
| 5,162,430 A | 11/1992 | Rhee et al. |
| 5,166,058 A | 11/1992 | Wang et al. |
| 5,171,217 A | 12/1992 | March et al. |
| 5,185,152 A | 2/1993 | Peyman |
| 5,187,076 A | 2/1993 | Wozney et al. |
| 5,192,741 A | 3/1993 | Orsolini et al. |
| 5,197,977 A | 3/1993 | Hoffman, Jr. et al. |
| 5,206,028 A | 4/1993 | Li |
| 5,227,157 A | 7/1993 | McGinity et al. |
| 5,231,169 A | 7/1993 | Constantz et al. |
| 5,250,584 A | 10/1993 | Ikada et al. |
| 5,268,167 A | 12/1993 | Tung |
| 5,268,178 A | 12/1993 | Calhoun et al. |
| 5,271,961 A | 12/1993 | Mathiowitz et al. |
| 5,278,201 A | 1/1994 | Dunn et al. |
| 5,278,202 A | 1/1994 | Dunn et al. |
| 5,281,419 A | 1/1994 | Tuan et al. |
| 5,284,470 A | 2/1994 | Beltz |
| 5,284,559 A | 2/1994 | Lim et al. |
| 5,288,496 A | 2/1994 | Lewis |
| 5,308,623 A | 5/1994 | Fues et al. |
| 5,320,624 A | 6/1994 | Kaplan et al. |
| 5,324,307 A | 6/1994 | Jarrett et al. |
| 5,324,520 A | 6/1994 | Dunn et al. |
| 5,350,580 A | 9/1994 | Muchow et al. |
| 5,360,610 A | 11/1994 | Tice et al. |
| 5,366,508 A | 11/1994 | Brekke |
| 5,366,733 A | 11/1994 | Brizzolara et al. |
| 5,366,734 A | 11/1994 | Hutchinson |
| 5,376,636 A | 12/1994 | Rutherford et al. |
| 5,415,532 A | 5/1995 | Loughnane et al. |
| 5,437,857 A | 8/1995 | Tung |
| 5,460,803 A | 10/1995 | Tung |
| 5,534,244 A | 7/1996 | Tung |
| 5,562,895 A | 10/1996 | Tung |
| 5,577,891 A | 11/1996 | Loughnane et al. |
| 5,656,153 A * | 8/1997 | Kameno et al. ................ 210/97 |
| 5,716,852 A | 2/1998 | Yager et al. |
| 5,725,776 A | 3/1998 | Kenley et al. |
| 5,744,042 A * | 4/1998 | Stange et al. ................ 210/645 |
| 5,798,042 A * | 8/1998 | Chu et al. ..................... 210/490 |
| 5,833,954 A | 11/1998 | Chow et al. |
| 5,855,562 A | 1/1999 | Moore et al. |
| 5,871,360 A | 2/1999 | Kato |
| 5,885,829 A | 3/1999 | Mooney et al. |
| 5,902,336 A | 5/1999 | Mishkin |
| 5,917,322 A | 6/1999 | Gershenfeld et al. |
| 5,932,100 A | 8/1999 | Yager et al. ................. 210/634 |
| 5,944,684 A | 8/1999 | Roberts et al. |
| 5,948,684 A | 9/1999 | Weigl et al. .................... 436/52 |
| 5,980,481 A * | 11/1999 | Gorsuch ....................... 604/28 |
| 5,984,891 A | 11/1999 | Keilman et al. |
| 5,993,786 A | 11/1999 | Chow et al. |
| 6,000,341 A | 12/1999 | Tung |
| 6,001,897 A | 12/1999 | Dickens |
| 6,056,930 A | 5/2000 | Tung |
| 6,114,408 A | 9/2000 | Dickens |

| | | |
|---|---|---|
| 6,117,100 A | 9/2000 | Powers et al. |
| 6,117,122 A | 9/2000 | Din et al. |
| 6,128,764 A | 10/2000 | Gottesman |
| 6,159,739 A * | 12/2000 | Weigl et al. .................. 436/52 |
| 6,187,838 B1 | 2/2001 | Dickens |
| 6,196,992 B1 | 3/2001 | Keilman et al. |
| 6,197,494 B1 | 3/2001 | Oberhardt |
| 6,206,959 B1 | 3/2001 | Dickens |
| 6,210,759 B1 | 4/2001 | Dickens |
| 6,281,256 B1 | 8/2001 | Harris et al. |
| 6,317,766 B1 | 11/2001 | Grover |
| 6,332,985 B1 | 12/2001 | Sherman et al. |
| 6,899,915 B2 | 5/2002 | Yelick et al. |
| 6,398,859 B1 | 6/2002 | Dickens et al. |
| 6,406,631 B1 | 6/2002 | Collins et al. |
| 6,413,498 B1 | 7/2002 | Malmagro |
| 6,432,630 B1 * | 8/2002 | Blankenstein .................. 435/4 |
| 6,459,097 B1 | 10/2002 | Zagoskin |
| 6,472,210 B1 | 10/2002 | Holy et al. |
| 6,488,896 B2 | 12/2002 | Weigl et al. |
| 6,504,172 B2 | 1/2003 | Zagoskin et al. |
| 6,511,814 B1 | 1/2003 | Carpenter |
| 6,527,735 B1 * | 3/2003 | Davankov et al. ............ 604/29 |
| 6,551,842 B1 | 4/2003 | Carpenter |
| 6,561,997 B1 | 5/2003 | Weitzel et al. |
| 6,563,311 B2 | 5/2003 | Zagoskin |
| 6,582,385 B2 * | 6/2003 | Burbank et al. ............ 604/5.04 |
| 6,585,682 B1 * | 7/2003 | Haraldsson et al. ........... 604/29 |
| 6,602,719 B1 | 8/2003 | Carpenter |
| 6,605,822 B1 | 8/2003 | Blais et al. |
| 6,614,047 B2 | 9/2003 | Tzalenchuk et al. |
| 6,670,630 B2 | 12/2003 | Blais et al. |
| 6,742,661 B1 | 6/2004 | Schulte et al. |
| 6,743,626 B2 | 6/2004 | Baum et al. |
| 6,758,975 B2 | 7/2004 | Peabody et al. |
| 6,784,451 B2 | 8/2004 | Amin et al. |
| 6,793,725 B2 | 9/2004 | Chow et al. |
| 6,796,955 B2 | 9/2004 | O'Mahoney et al. |
| 6,803,599 B2 | 10/2004 | Amin et al. |
| 6,897,468 B2 | 5/2005 | Blais et al. |
| 6,900,456 B2 | 5/2005 | Blais et al. |
| 6,911,664 B2 | 6/2005 | Il'ichev et al. |
| 6,930,320 B2 | 8/2005 | Blais et al. |
| 7,002,174 B2 | 2/2006 | Il'ichev et al. |
| 7,052,907 B2 | 5/2006 | Shi et al. |
| 7,118,676 B2 | 10/2006 | Mueth et al. |
| 7,150,834 B2 | 12/2006 | Mueth et al. |
| 7,309,232 B2 | 12/2007 | Rutherford et al. |
| 7,309,323 B2 | 12/2007 | Gura et al. |
| 7,351,218 B2 | 4/2008 | Bene |
| 2001/0048637 A1 * | 12/2001 | Weigl et al. .................. 366/341 |
| 2001/0055546 A1 * | 12/2001 | Weigl et al. .................. 422/100 |
| 2002/0052571 A1 | 5/2002 | Fazio |
| 2002/0090644 A1 | 7/2002 | Weigl et al. |
| 2002/0159920 A1 * | 10/2002 | Weigl ......................... 422/100 |
| 2002/0172622 A1 | 11/2002 | Weigl et al. |
| 2003/0034306 A1 | 2/2003 | Schulte et al. |
| 2004/0009096 A1 * | 1/2004 | Wellman ..................... 422/44 |
| 2004/0016918 A1 | 1/2004 | Amin et al. |
| 2004/0045891 A1 * | 3/2004 | Gilbert et al. .......... 210/321.65 |
| 2004/0069708 A1 * | 4/2004 | Laurell et al. ................ 210/646 |
| 2004/0082903 A1 * | 4/2004 | Micheli ....................... 604/29 |
| 2004/0225249 A1 | 11/2004 | Leonard et al. |
| 2004/0245102 A1 * | 12/2004 | Gilbert et al. ............... 204/451 |
| 2005/0082210 A1 * | 4/2005 | Favre ........................ 210/109 |
| 2005/0101901 A1 * | 5/2005 | Gura ........................ 604/5.02 |
| 2005/0121604 A1 * | 6/2005 | Mueth et al. ................ 250/251 |
| 2005/0178727 A1 * | 8/2005 | Takagi et al. ............... 210/634 |
| 2005/0201903 A1 * | 9/2005 | Weigl et al. ................ 422/100 |
| 2005/0202563 A1 * | 9/2005 | Dasgupta et al. .............. 436/52 |
| 2006/0076295 A1 | 4/2006 | Leonard et al. |
| 2007/0029257 A1 | 2/2007 | Mueth et al. |

FOREIGN PATENT DOCUMENTS

| | | |
|---|---|---|
| JP | 10-507962 | 8/1998 |
| JP | 11-508182 | 7/1999 |
| JP | 2000-512541 | 9/2000 |
| JP | 2001-511520 | 8/2001 |
| JP | 2002-509248 | 3/2002 |
| WO | WO 02/36246 | 5/2002 |
| WO | WO 02/45813 | 6/2002 |
| WO | WO 02/062454 | 8/2002 |

OTHER PUBLICATIONS

Goldsmith, H.L. et al., "Margination of Leukocytes in Blood Flow through Small Tubes," Microvasc. Res. 1984, 27(2):204-222.
Takayama et al, "Topographical Micropatterning of Poly(dimethylsiloxame) Using Lamimar Flows of Liquids in Capillaries," Adv. Materials, 2001, pp. 570-574.
Leonard et al., "Dialysis without Membranes: How and Why?," Blood Purification 22(1) 2004, pp. 92-100.
PCT/US2006/018008—International Search Report dated Jul. 27, 2007.
PCT/US2004/007966—International Search Report dated Dec. 28, 2005.
U.S. Appl. No. 60/557,750, filed Mar. 29, 2004, Grajcar et al.
U.S. Appl. No. 60/557,747, filed Mar. 29, 2004, Amin et al.
U.S. Appl. No. 60/556,778, filed Mar. 26, 2004, Hilton et al.
U.S. Appl. No. 60/372,958, filed Apr. 15, 2002, Il'chev et al.
U.S. Appl. No. 60/349,663, filed Jan. 15, 2002, Amin et al.
U.S. Appl. No. 60/341,974, filed Dec. 18, 2001, Il'ichev et al.
Abbitt, K.B, Nash, G.B., "Rheological Properties of the Blood Influencing Selectin-Mediated Adhesion of Flowing Leukocytes." PresS. Am J Physiol Heart Circ Physiol, Mar. 2003, 285: pp. H229-H240.
Blackshear, P.L., "Two New Concepts That Might Lead To A Wearable Artificial-Kidney." Kidney International, 1978: pp. S133-S137.
Giddings, J.C., "Continuous Separation In Split-Flow Thin (Splitt) Cells Potential Applications To Biological Materials." Separation Science And Technology, 1988, 23(8& 9) : pp. 931-943.
Goldsmith, H.L., Spain, S., "Margination of Leukocytes in Blood Flow Through Small Tubes." Microvasc. Res., Mar. 1984, 27(2): pp. 204-222.
Harper, G., "Home Hemodialysis: A Patients's Perspective." Home Hemodial Int., 1997, 1: pp. 8-11.
Henne, W. et al, "A Wearable Artificial-Kidney." Artificial Organs, 1977, 1(1): p. 126.
Leonard, E.F., Cortell, S., Vitale N.G., "Membraneless Dialysis- Is It Possible?" Contrib Nephrol. 2005, 149: pp. 343-353.
Levin, S., Tawil, G., "Analytical Splitt Fractionation In The Diffusion Mode Operating as a Dialysis-Like System Devoid of Membrane—Application To Drug-Carrying Liposomes." Analytical Chemistry, 1993, 65(17): pp. 2254-2261.
Neff, M.S., Sadjadi, S. Slifkin, R., "A Wearable Artificial Glomerulus." Trans Am Soc Artif Intern Organs, 1979, 25: pp. 71-73.
Ronco, C., "Microfluidic, Membrane-Free Dialysis." American Society of Nephrology, Annual Meeting. 2002.
Schmuhl. R. et al., "Si-Supported Mesoporous and Microporous Oxide Interconnects as Electrophoretic Gates for Application in Microfuidic Devices." Analytical Chemistry, Jan. 2005, 77(1): pp. 178-184.
Seo, S. et al., "Improvement Of The Wearable Artificial Kidney." International Journal of Artificial Organs, 1981, 5(3): pp. 321.
Singh, M., Ramesh, A.T.V., "Haematocrit Dependence Of Cellular Axial Migration And Tubular Pinch Effects In Blood Flow Through Glass Capillaries." Current Science, Feb. 1990, 59(4): pp. 223-226.
Takayama, S. et al., "Topographical Micropatterning of Poly(diethylsiloxame) Using Laminar Flows of Liquids in Capillaries." Adv. Materials, Apr. 201, 13(8): pp. 570-574.
VanHolder, R., Ringoir S., "Pitfalls O Wearable Artificial-Kidney." International Journal Of Artificial Organs, 1990, 13(11): pp. 715-719.
Takai et al., "A New Treatment Strategy Using Both Intermittent Short Dialysis and Continuous Ambulatory Hemofiltration," Transactions of the American Society for Artificial Internal Organs, 1991, 37(3):pp. M325-M327.

* cited by examiner

SYSTEMS AND METHODS OF BLOOD-BASED THERAPIES HAVING A MICROFLUIDIC MEMBRANELESS EXCHANGE DEVICE

CROSS REFERENCE TO RELATED APPLICATIONS

The application is a divisional of U.S. application Ser. No. 10/801,366, filed Mar. 15, 2004, pending, which claims the benefit of U.S. Provisional Application Ser. No. 60/454,579, filed Mar. 14, 2003, expired, both of which are hereby incorporated by reference in their entireties.

FIELD OF THE INVENTION

Generally speaking, the present invention relates to the purification of a sample fluid. More particularly, the present invention relates to the purification of a sample fluid, blood fluid) by selectively removing components using a microfluidic membraneless exchange device.

BACKGROUND OF THE INVENTION

Extracorporeal processing of blood is known to have many uses. Such processing may be used, for example, to provide treatment of a disease. Hemodialysis is the most commonly employed form of extacorporeal processing for this purpose. Additional uses for extracorporeal processing include extracting blood components useful in either treating others or in research. Apheresis of plasma (i.e., plasmaphesis) and thrombocytes, or platelets, are the procedures most commonly employed for this purpose.

Many different extracorporeal blood processing processes have been developed, each of which seeks to remove certain components from the blood, depending on the reason for processing the blood. (It will be understood that as used herein, blood, or blood fluid, refers to any fluid having blood components from which extraction of certain components, such as toxins or albumin, is desired.) The most common process utilizes an artificial membrane of substantial area, across which selected blood components are induced to flow. This flow is generally induced by a transmembrane difference in either concentration or pressure, or a combination of the two. Another form of blood processing calls for the separation of certain components from blood by passing the blood over sorbent particles. In yet other forms of blood processing, not practiced as commonly, blood is directly contacted with an immiscible liquid (e.g., a fluorocarbon liquid), with the desired result being the removal of dissolved carbon dioxide and the provision of oxygen. The usefulness of blood processing techniques employing immiscible liquids is limited, however, because these immiscible liquids generally have very limited capacity to accept the blood components that it is desirable to extract.

One common example of a therapeutic use for blood processing is the mitigation of the species and volume imbalances accompanying end-stage renal disease. The population of patients treated in this manner (i.e., through hemodialysis) exceeds 260,000 and continues to grow, with the cost of basic therapy exceeding $5 billion per year excluding complications. The overwhelming majority of these patients (about 90%), moreover, are treated in dialysis centers, generally in thrice-weekly sessions. While procedures have been—and continue to be—refined, the components and the geometry of hemodialysis were largely fixed in the 1970's: a bundle of several thousand, permeable hollow fibers, each about 25 cm long and about 200 μm internal diameter, perfused externally by dialyzing solution, with the device operated principally in a diffusive mode but with a transmembrane pressure applied to induce a convective outflow of water. Upward of 120 liters per week of patient blood are dialyzed against upwards of 200 liters per week of dialyzing solution, often in three weekly treatments that total as little as seven to nine hours per week. These numbers vary somewhat, and competing technologies exist, but the basic approach just described predominates.

Despite the benefits of therapies (e.g., hemodialysis) using the various forms of blood processing described above, the prolongation of life achieved is complicated by the progression and complexity of the disease the therapies are used to treat (few patients on dialysis are ever completely rehabilitated), and by several problems that are innate to the therapies themselves. For example, problems arise with blood processing as a result of the contact of blood with extensive areas of artificial membrane (as in the case of hemodialysis), and well as the contact of blood with sorbents or immiscible fluids as described above. In particular, this contact often induces biochemical reactions in the blood being processed, including the reactions that are responsible for clotting, activation of the complement systems, and irreversible aggregation of blood proteins and cells.

Another problem associated with known blood processing techniques is that the contact of blood with an artificial membrane (or another medium, such as a sorbent or immiscible fluid) is likely to cause the blood-medium interface to become fouled. It is generally known that therapeutic interventions (e.g., those related to end-stage renal disease) are optimally conducted with slow delivery and in as nearly a continuous fashion as possible, in emulation of the continuous action of a natural kidney. However, fouling caused by the contact of blood with the medium limits the time that a device which contains these interfaces can be usefully employed. As a result, portable blood processing devices become impractical, and patients are generally forced to undergo the type of episodic dialysis schedule described above, which creates many negative side effects such as physical exhaustion and excessive thirst. Moreover, even while daily dialysis (e.g., 1.5-2.0 hours, six days per week) or nocturnal dialysis (e.g., 8-10 hours, 6-7 nights per week) improves this situation by extending treatment times, a patient using one of these forms of treatment is still required to remain near a hospital or clinical facility that can administer the dialysis procedure.

In light of the above, it would be desirable to provide techniques for processing blood in which treatment times are extended (with consequently lower rates of flow) and that do not require a patient to remain near a hospital or clinic. Moreover, it would also be desirable to provide techniques for processing blood that eliminate (or at least reduce) the inducement of undesirable biochemical reactions, and where the blood-medium interfaces do not become fouled.

SUMMARY OF THE INVENTION

The above and other deficiencies associated with existing blood processing processes are overcome in accordance with the principles of the present invention which are described below. According to one aspect of the invention, a membraneless exchange device for extracting components from a sample fluid is described which includes first, second and third inlet channels, first, second and third exit channels and a microfluidic extraction channel connected to the first, second and third inlet channels and the first, second and third exit channels. Moreover, laminar flows of a first extractor fluid, the sample fluid, and a second extractor fluid are established inside the extraction channel, and sheathing of the sample fluid by the first and second extractor fluids substantially limits contact between the sample fluid and the surfaces of the extraction channel.

According to another embodiment of the present invention, a system for performing hemodialysis is provided which includes a membraneless exchange device including first and second dialysate inlet channels, blood inlet and exit channels, first and second dialysate exit channels and a microfluidic dialysis channel connected to the first and second dialysate inlet and outlet channels and the blood inlet and exit channels. Moreover, laminar flows of a first dialysate fluid, blood fluid, and a second dialysate fluid are established in order inside the dialysis channel, and at least some of the components of the blood fluid exits the device through the first and second dialysate exit channels. Additionally, according to the invention, a secondary processor receives the dialysate fluid and the at least some of the components of the blood fluid exiting the device through the first and second dialysate exit channels.

In yet another embodiment of the present invention, a method for extracting components from a sample fluid is provides which includes establishing laminar flows of a first extractor fluid, the sample fluid and a second extractor fluid inside a microfluidic extraction channel. Sheathing of the sample fluid by the first and second extractor fluids, moreover, substantially limits contact between the sample fluid and the surfaces of the extraction channel. The method further includes withdrawing the first extractor fluid, the sample fluid and the second extractor fluid from the extraction channel such that at least a portion of the sample fluid is removed together with the first extractor fluid and the second extractor fluid and apart from the remainder of the sample fluid.

A method for performing hemodialysis is also provided which includes establishing laminar flows of a first dialysate fluid, blood fluid and a second dialysate fluid inside a microfluidic extraction channel, withdrawing the first dialysate fluid, the blood fluid and the second dialysate fluid from the extraction channel such that at least some of the components of the blood fluid are removed together with the first dialysate fluid and the second dialysate fluid and apart from the remainder of the blood fluid, and providing the first and second dialysate fluids and the at least some of the components of the blood fluid to a secondary processor.

In general, however, the present invention is directed toward microfluidic membraneless exchange devices and systems, and methods of making the same, for selectively removing undesirable materials from a sample fluid (e.g., blood fluid) by contact with a miscible fluid (extractor fluid or secondary fluid, e.g., dialysate). A microfluidic device, as considered in this application, has channels whose height is less than about 0.6 mm, where "height" is the dimension perpendicular to the direction of flow and also perpendicular to the interfacial area across which transport occurs. For example, flow patterns and species exchanges occur when blood is flowed as a thin layer adjacent to, or between, concurrently flowing layers of a secondary fluid, without an intervening membrane. The secondary fluid, moreover, is generally miscible with blood and diffusive and convective transport of all components is expected. The following reference which refers to membraneless devices described below is hereby incorporated by reference in its entirety: Leonard et al., Dialysis without Membranes: How and Why?, Blood Purification 22 (1) 2004 92-100.

Sheathing a core of blood with the miscible fluid, or assuring that the miscible fluid lies between at least a substantial portion of the blood and the enclosing boundaries of the flow path, prevents or at least limits contact of the blood with these boundaries. In turn, this configuration of the two fluids prevents or at least reduces the undesirable activation of factors in the blood, thereby minimizing bioincompatibilities that have been problematic in prior techniques of blood processing.

The invention also eliminates or at least substantially reduces the fouling reactions that have been known to be a major deterrent to the continuous use of an extracorporeal extraction device. In particular, as the primary transport surface in the membraneless exchange device (also referred to herein as a membraneless separator) of the invention is intrinsically non-fouling, a major deterrent to long-term or continuous operation is removed, opening the possibility to the design and construction of small, wearable devices or systems with the recognized benefits of nearly continuous blood treatment. Such a device or system could be very small and worn or carried by the patient (e.g., outside of a hospital or clinic setting), and could be supplied with external buffer reservoirs (in a back-pack, briefcase, or from a reservoir located in the home, located at the place of work, etc.). Further, because fouling would be reduced, and sustained operation at low blood flows over long times would be allowed, such anticoagulation as might be required is likely to have an effect confined to the extracorporeal circuit. As understood by those skilled in the art, avoiding systemic anticoagulation outside of the clinic is highly desirable.

The devices, systems and methods of the invention described herein also have the benefit of being capable of diffusing various blood components having different sizes. In particular, the flow of blood and a miscible fluid with which it is in contact can be controlled for the purpose of achieving the desired separation of components (e.g., separating molecules of low molecular weight only). For example, as explained below, various flow conditions may be used that cause blood cells to move away from the blood-liquid interface, thereby making it is possible to "skim" blood in order to remove substantial amounts of plasma, without cells.

As also discussed below, membraneless contact of a thin layer of blood with a sheathing fluid according to the present invention may be used to cause high rates of exchange per unit area of blood-sheathing fluid contact for all solutes, but with a discrimination among free (unbound) solutes that is less than the square-root of the ratio of their diffusion coefficients. Moreover, while high exchange rates (e.g., of toxic substances) are often desirable, indiscriminate transport is not. Therefore, according to the principles of the present invention, a membraneless exchange device as described herein is used in conjunction with at least one secondary processor (e.g., a membrane device or other type of separator) in order to restrict the removal of desirable substances and effect the removal of undesirable substances from blood. The efficiency of such a secondary separator is greatly increased by the use of the primary separator that is capable of delivering cell-depleted (or cell-free) fractions of blood to it. Therefore, according to another aspect of this invention, transport of molecular components of blood to the sheathing fluid may be indiscriminate. The sheathing fluid, carrying both those molecular components which it is, and is not, desirable to remove from blood, is provided to the secondary separator, such that the fluid entering the secondary separator is substantially cell-free. The secondary separator, meanwhile, regulates the operation of the membraneless separator through the composition of the recycle stream that it returns (directly or indirectly) to the sheath fluid inlets of the membraneless separator. According to the principles of the present invention, moreover, a membrane-based secondary separator used in this manner is able to achieve much higher separation velocities because concentration polarization (i.e., the accumulation of material rejected by the secondary separator on the upstream side of the separator) is limited to proteins and does not involve cells. Moreover, because cells would be retained in the primary separator (i.e., the membraneless exchange device), they would see artificial material only on its conduit surfaces, not on its liquid-liquid contact area, whence bioincompatibilities should be much reduced. As such, it should be understood that the need for anticoagulation may be greatly reduced or eliminated.

Further features of the invention, its nature and various advantages, will be more apparent upon consideration of the following detailed description, taken in conjunction with the accompanying drawings, in which like reference characters refer to like parts throughout.

DETAILED DESCRIPTION OF THE INVENTION

Figure 1:
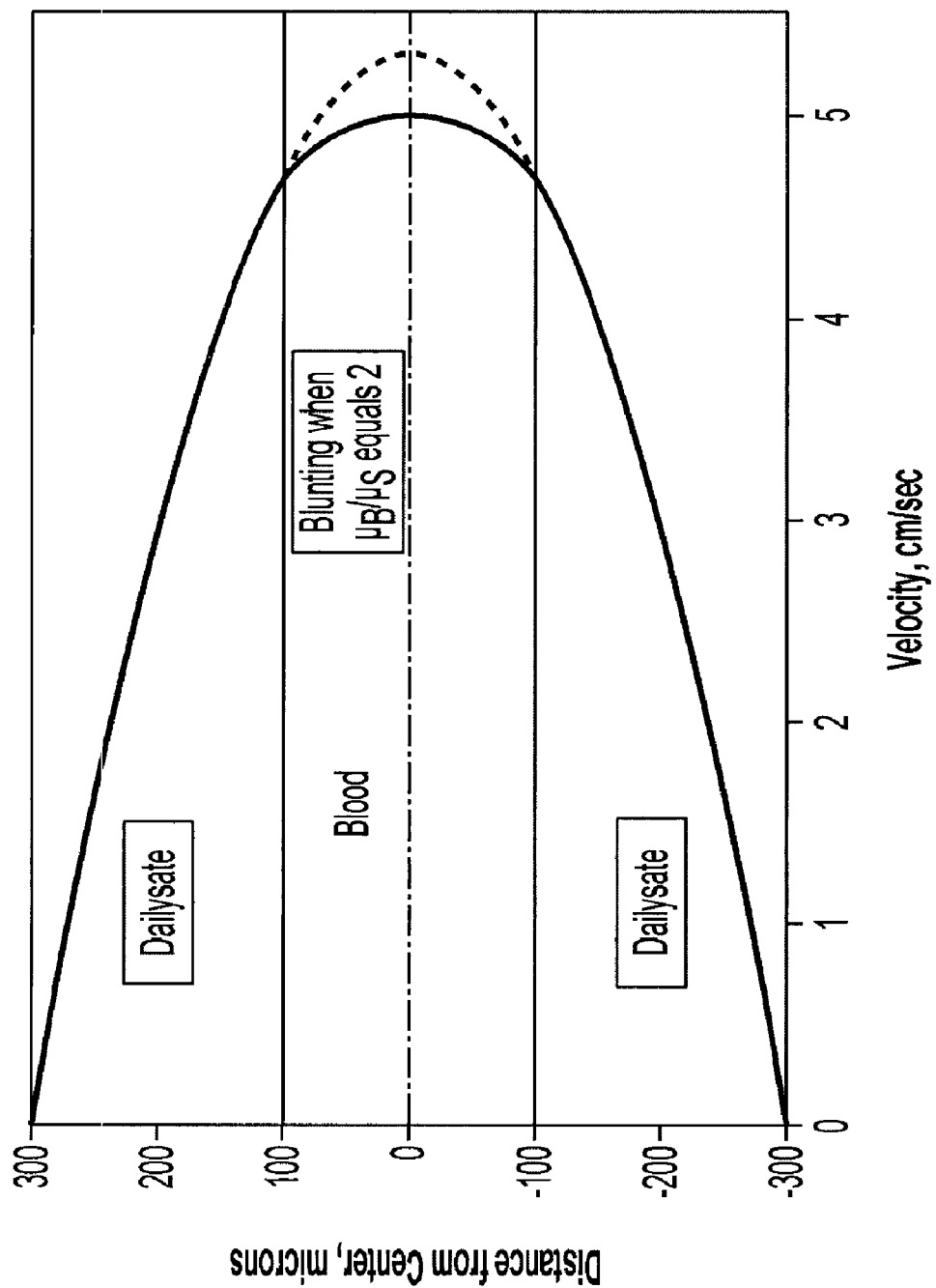
FIG. 1 shows the velocity profile of a core stream of blood sheathed on both of its sides by a dialysate fluid calculated for blood with a viscosity assumed twice that of the dialysate fluid and with a centerline velocity of 5 cm/sec.

According to one aspect of the invention, a membraneless exchange device for extracting components from a sample fluid is described which includes first, second and third inlet channels, first, second and third exit channels and a microfluidic extraction channel connected to the first, second and third inlet channels and the first, second and third exit channels. Moreover, laminar flows of a first extractor fluid, the sample fluid, and a second extractor fluid are established inside the extraction channel, and sheathing of the sample fluid by the first and second extractor fluids substantially limits contact between the sample fluid and the surfaces of the extraction channel. In one embodiment of the device, at least 90% of the sample fluid is sheathed by the first and second extractor fluids. In other embodiments, 95% of the sample fluid is sheathed. In yet other embodiments, at least a portion of the sample fluid exits the device with the first extractor fluid through the first exit channel, and advective transport of molecules within said extraction channel is substantially nonexistent. The composition of the first extractor fluid, moreover, is substantially the same as the composition of the second extractor fluid is various embodiments. In other preferred embodiments, the sample fluid flow is between the first and second extractor fluid flows. Moreover, a first diverter is formed from a portion of the first exit channel and a portion of the second exit channel, while a second diverter is formed from a portion of the second exit channel and a portion of the third exit channel. It should also be understood that the device may include a first interface formed between the first extractor fluid flow and the sample fluid flow that is aligned with at least a portion of the first diverter, and may also include a second interface formed between the second extractor fluid flow and the sample fluid flow that is aligned with at least a portion of the second diverter. In various embodiments of the invention, moreover, the sample fluid is blood fluid, in which case it is contemplated that the components extracted from the sample fluid are non-cellular components of the blood fluid. Additionally, the device may use a first pump for controlling the flow of extractor fluid in the extraction channel, and may use a second pump for controlling the flow of sample fluid in the extraction channel. When a first pump is used, it may be an injection pump that controls the flow of extractor fluid into the extraction channel, and a withdrawal pump may be used that controls the flow of extractor fluid out of the extraction channel. In various embodiments, additionally, a source of extractor fluid is connected to said first inlet channel and a source of sample fluid connected to said second inlet channel. It will be understood that the source of sample fluid can be, for example, a human being. In preferred embodiments, moreover, the extraction channel of the device according to the invention has a height of less than 600 µm, and has a width-to-height ratio of at least ten. The device may also be used in a system for extracting components from a sample fluid, where the system also includes a secondary processor that receives the first extractor fluid, the second extractor fluid and at least some of the components of the sample fluid upon exiting the extraction channel. It will be understood that the secondary processor may be, for example, a membrane device or a sorption device.

According to another embodiment of the present invention, a system for performing hemodialysis is provided which includes a membraneless exchange device including first and second dialysate inlet channels, blood inlet and exit channels, first and second dialysate exit channels and a microfluidic dialysis channel connected to the first and second dialysate inlet and outlet channels and the blood inlet and exit channels. Moreover, laminar flows of a first dialysate fluid, blood fluid, and a second dialysate fluid are established in order inside the dialysis channel, and at least some of the components of the blood fluid exits the device through the first and second dialysate exit channels. Additionally, according to the invention, a secondary processor receives the dialysate fluid and the at least some of the components of the blood fluid exiting the device through the first and second dialysate exit channels. In various embodiments, the secondary processor filters the dialysate fluid and the at least some of the components of the blood fluid exiting the device through the first and second dialysate exit channels, and returns the filtered fluid to the first and second dialysate inlet channels. In certain preferred embodiments, these components of the blood fluid are substantially non-cellular components of the blood fluid. In other embodiments, sheathing of the blood fluid by the first and second dialysate fluids substantially limits contact between the blood fluid and the surfaces of the dialysis channel. Moreover, the secondary processor may be a membrane device, or may be a sorption device, for example. It will also be understood that the composition of the first dialysis fluid may be substantially the same as the composition of the second dialysis fluid. According to other aspects of the invention, meanwhile, a first diverter is formed from a portion of the first dialysate exit channel and a portion of the blood exit channel, and a second diverter is formed from a portion of the blood exit channel and a portion of the second dialysate exit channel. A first pump for controlling the flow of dialysate fluid in the dialysis channel and a second pump for controlling the flow of blood fluid in the dialysis channel may also be used in accordance with the principles of the present invention. According to several embodiments, the interface between the first dialysate fluid and the blood fluid is varied by adjusting the velocities of the laminar flows of the first dialysate fluid and the blood fluid. In other embodiments, the interface between the blood fluid and the second dialysate fluid is varied by adjusting the velocities of the laminar flows of the blood fluid and the second dialysate fluid. A reservoir for storing a viscosity agent may also be used in the system, where the viscosity agent is mixed with the first and second dialysate fluid to alter the viscosity of the first and second dialysate fluid. Additionally, a detector for detecting a presence of an undesired blood component within the dialysate fluid upon exiting the dialysis chamber may be used. In this case, for example, the detector is a photo detector. According to another aspect of the invention, a first pump for controlling the flow of dialysate fluid in the dialysis channel is adjusted based on said detected presence of an undesired blood component within said dialysate fluid. Moreover, for example, the velocities of the laminar flows of the first dialysate fluid, the blood fluid and the second dialysate fluid are adjusted based on the detected presence of an undesired blood component within the first and second dialysate fluids according to the invention. Additionally, according to the invention, the first and second dialysate fluids may include at least one of the following: a hyper osmolar solution, a solution high in glucose content, or a polyelectrolye osmotic agent.

In yet another embodiment of the present invention, a method for extracting components from a sample fluid is provides which includes establishing laminar flows of a first extractor fluid, the sample fluid and a second extractor fluid inside a microfluidic extraction channel. Sheathing of the sample fluid by the first and second extractor fluids, moreover, substantially limits contact between the sample fluid and the surfaces of the extraction channel. The method further includes withdrawing the first extractor fluid, the sample fluid and the second extractor fluid from the extraction channel such that at least a portion of the sample fluid is removed together with the first extractor fluid and the second extractor fluid and apart from the remainder of the sample fluid. According to the invention, moreover, establishing laminar flows includes providing first, second and third inlet channels and providing first, second and third exit channels. Additionally, for example, the method includes providing the first and second extractor fluids and the at least a portion of the sample fluid to a secondary processor.

A method for performing hemodialysis is also provided which includes establishing laminar flows of a first dialysate fluid, blood fluid and a second dialysate fluid inside a microfluidic extraction channel, withdrawing the first dialysate fluid, the blood fluid and the second dialysate fluid from the extraction channel such that at least some of the components of the blood fluid are removed together with the first dialysate fluid and the second dialysate fluid and apart from the remainder of the blood fluid, and providing the first and second dialysate fluids and the at least some of the components of the blood fluid to a secondary processor. In various embodiments, the method also includes using the secondary processor to filter the first and second dialysate fluids and the at least some of the components of the blood fluid, as well as returning the filtered fluid from the secondary processor to the extraction channel. In yet other embodiments, the method includes sheathing the blood fluid by the first and second dialysate fluids to substantially limit the contact between the blood fluid and the surfaces of the dialysis channel.

Referring to FIG. 1, calculated for blood with a viscosity assumed twice that of the sheathing fluid and with a centerline velocity of 5 cm/sec, a flow path length of 10 cm would result in a contact time of slightly longer than 2 sec. The steady contact of two moving liquids for an exposure time determined by the length of their contact area divided by their interfacial velocity ($\tau=L/v$) is highly analogous to the sudden exposure of one volume of stagnant fluid to another for a specified time. Thus, what happens to the flowing fluids along their shared flow path is comparable to what would happen to two stagnant fluids over their exposure time to each other. The stagnant fluid problem was solved by Loschmidt in 1870.

$$E = \frac{1}{2} - \frac{4}{\pi^2} \sum_0^\infty \frac{1}{(2n+1)^2} \exp\left[-(2n+1)^2 \left(\frac{\pi}{2B}\right)^2 Dt\right]$$

for which the zeroth order term, $$E = \frac{1}{2} - \frac{4}{\pi^2} \exp\left(-\left[\frac{\pi}{2B}\right]^2 Dt\right),$$

suffices when $$\left(\frac{\pi}{2B}\right)^2 Dt > 0.7.$$

This formula greatly simplifies the estimation of how much mass can be transferred between fluids in a membraneless system. In particular, this formula provides an approximation of the extraction E of a component with a diffusion coefficient D when two liquids flow side-by-side and remain in contact for an interval of time, t.

Figure 2:
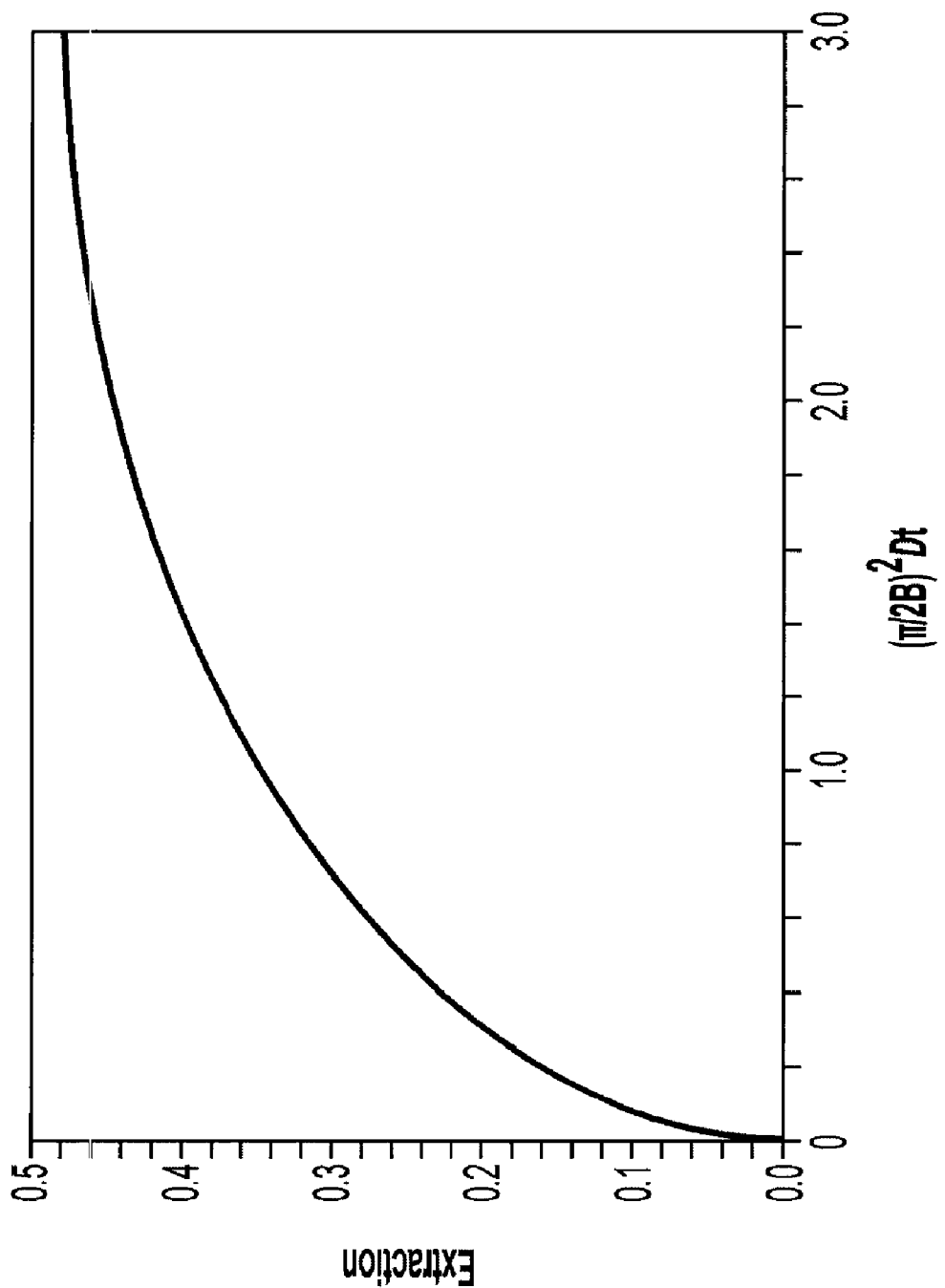
FIG. 2 shows a plot using Loschmidt's formula of 1870, where each fluid layer has the same thickness.

FIG. 2, meanwhile, shows a plot using a version of Loschmidt's formula, where each fluid layer has the same thickness B (i.e., B is the half-thickness of the sheathed layer of sample fluid). The situation shown in the plot of FIG. 2 can be interpreted as a blood layer, of thickness B, contacting a layer of sheathing fluid (i.e., extractor fluid). The sheathing layer is presumed to be at zero concentration and E is the fraction of material in the blood layer that is extracted in a time t, where D is the diffusion coefficient of the extracted substance. If a layer of thickness twice B is bounded on both sides by fluid layers of thickness B, the formula still applies, as written. As indicated by this formula, E cannot exceed ½ since the prescription of concurrent flow allows, at best, the two fluids to come to equilibrium.

For example, if one prescribes 90% of maximum extraction (E=0.45), the ratio $Dt/B^2$ must be approximately 0.86. Any combination of diffusivity, layer thickness, and exposure time that produces this value will produce the same extraction. Moreover, it can be shown that the necessary area (2LW) to achieve this extraction equals 0.86 BQ/D, where Q is the blood (and sheath fluid) flow rate. Thus, for urea (D=$10^{-5}$ cm$^2$/sec) at a blood flow rate of 0.3 cm$^3$/sec, the required area is 2.57 B $10^4$ cm$^2$. If B is taken to be 100 μm, the required area is 257 cm². This flow corresponds to what might be needed in a wearable artificial kidney. If, instead, a conventional flow of 5 cm³/sec were used, the required area would be 4300 cm². Thinner films, moreover, would require less area but would result in higher shear rates and pressure gradients. In terms of extraction, any combination of length L and width W that produces the requisite area is equivalent. (If one assumes D for albumin to be $5 \cdot 10^{-7}$ cm²/sec, its extraction would be 0.116, 26% of that for urea, unchangeable at this extraction level for urea).

It should be noted that use of the Loschmidt formula with flowing systems introduces an incongruity that prevents precise estimation of mass transfer rates and clearances, given that it presumes that both fluids are moving at uniform velocity. In particular, it provides an excellent approximation for the sheathed fluid (blood), but ignores the nearly linear decay in velocity with distance from the interface in the sheathing fluid. Nevertheless, the Loschmidt formula is adequate for design purposes when the sheathing layer has a total thickness (2B) that is twice that of its half of the blood layer (as shown in FIG. 1), and thus a rate of flow nearly equal to its half of the central stream.

The shear-induced self-diffusion coefficient of cells, meanwhile, can be estimated by using the expression of Leighton and Acrivos (1987) for concentrated suspensions: $D_{particle} \propto \phi^2 \alpha^2 \gamma^2$, where $\phi$ is the particle volume fraction, $\alpha$ is the particle radius, and $\gamma$ is the shear rate. Then, the characteristic displacement of a cell can be expressed as $\Delta y \propto \sqrt{D_{particle} t}$. Choosing representative values for the layered flow system such that the cell volume fraction $\phi \cong 0.45/2 = 0.225$, the average radius a of the red blood cell $\cong 2.5$ μm, and the average shear rate $\dot{\gamma}$ over the blood layer $\cong 3$ to 28 s$^{-1}$ (based on an average velocity range of 0.5 to 5 cm/s), we calculate that $D_{particle} \sim 10^{-8}$ cm²/s, which is approximately three orders of magnitude smaller than the typical diffusion coefficient of small solutes. Based on this value of the shear-induced diffusion coefficient (and assuming 10 sec of contact between layers), it is estimated that blood cells are displaced by a characteristic distance $\Delta y \cong 3$ to 9 μm from the central layer, depending on the choice of blood velocity and the concomitant shear rate. As explained in greater detail below, this low distance of cell migration away from the central layer facilitates the removal of cell-free portions of blood by the membraneless separators described herein.

It should be noted that, according to one aspect of the present invention, the removing of undesirable materials from a sample fluid occurs under conditions that prevent advective mixing of blood and the secondary fluid. In its general usage herein, advection is used to describe the transport of fluid elements from one region to another, and is used to distinguish disordered convection from diffusion unaided by convection or diffusion in the presence of only ordered and unidirectional convection. The term advection is therefore used to mean a form of transport within a fluid or between two contacting miscible fluid in which clumps of fluid from two different positions are effectively interchanged. Advection, so defined, can occur in turbulent flows or in unstable laminar flows. Advective mixing, moreover, is often purposefully induced by the application of a moving agitator blade to a fluid. The prevention of advective mixing and the short contact times that lead to small areas of contact (and, in turn, to a small device that has a small size and a limited extracorporeal blood volume) is greatly facilitated by the use of a microfluidic geometry. An increase in channel height raises requisite contact time and tends to reduce the stability of the sheathed flow. When total blood layer thickness is 25, 50, or 100 μm, and the blood flow is 20 ml/min (as it might be with a wearable artificial kidney), the interfacial area needed to cause a substance such as urea (D=10$^{-5}$ cm²/sec) to reach 90% of equilibrium is, respectively, 18, 36, and 71 cm².

As mentioned above, the devices, systems and methods of the present invention allow the purification of blood without the use of a membrane by contact of the blood with a miscible fluid under conditions that prevent advective mixing. It will be clear from the detailed description of various embodiments of the invention provided below that the invention is useful in hemodialysis, for example. However, it should also be noted, and understood by those skilled in the art, that the present invention is also useful in other situations where a sample fluid is to be purified via a diffusion mechanism against another fluid (e.g., an extractor fluid).

According to the principles of the present invention, the purification techniques described herein enable the flow of blood, completely or partially surrounded by another liquid (e.g., extractor fluid) such that the streams are contacted in a small channel and are subsequently separated at the end of the channel. The middle stream is, thus, the blood to be purified, while the surrounding stream (or streams) is the extractor fluid. This membraneless contact, or sheathing of blood with layers of a miscible fluid, according to principles of the present invention, may occur along a flow path whose cross-section is either rectangular, preferably of great breadth and limited thickness, or circular. The invention is not limited in this manner.

Persons skilled in the art will appreciate that the requisite transport areas, moreover, can be achieved by combinations of channel length, width, and number according to the principles of the present invention. In particular, Area=2 (top and bottom)×width×length×number of channels stacked or otherwise arrayed in parallel. (As used herein, the term "width" refers to a dimension perpendicular to the direction of flow and parallel to the interface between the two liquids, while, as explained above, the term "height" refers to a dimension perpendicular to the direction of flow and also perpendicular to the interface between the two fluids). It is shown herein that the competing requirements of small height (to avoid excessive diffusion times and in-process volumes), short length (to avoid excessive pressure drop) and practical limitations on width of a single device, which suggests the need to array them in parallel, side-by-side or in a stack can be satisfied in practical microfluidic devices.

Figure 3:
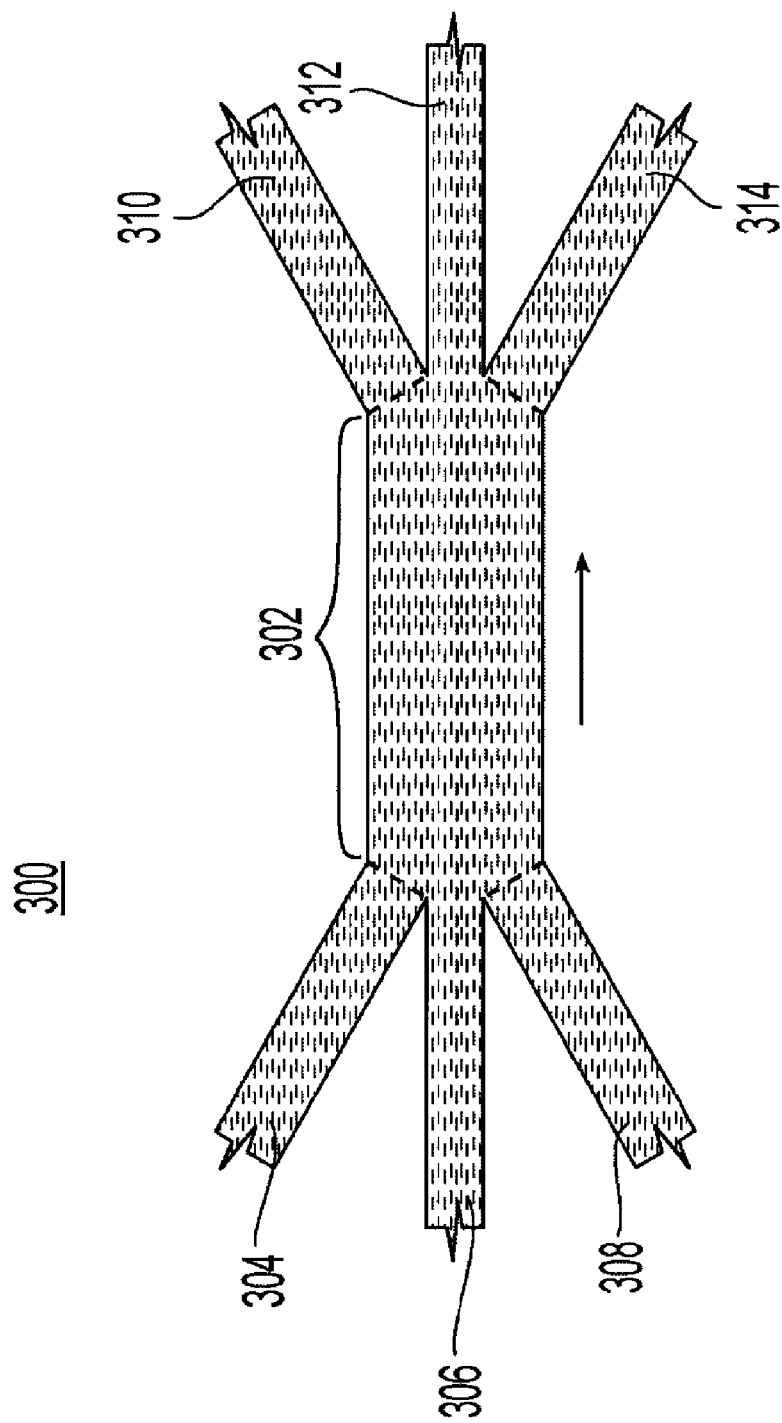
FIG. 3 shows a simplified view of a membraneless separator constructed in accordance with the principles of the present invention.

FIG. 3 shows a simplified view of a membraneless separator 300 fabricated in flat-sheet configuration in accordance with the principles of the present invention. According to one embodiment of the present invention, three flat strips of copper foil, each three centimeters wide, four centimeters long and 100 microns thick, are soldered in their mid-sections to form extraction channel 302. The ends (one centimeter) of the outer pieces are bent 30 degrees outward to form three separate inlet channels 304, 306 and 308 and three corresponding exit channels 310, 312 and 314 as shown in FIG. 3. According to the invention, the pieces are then coated with a mold release agent, and the channel is then placed in a Petri dish. At this time, an amount of PDMS precursor/curing agent mixture (10:1 ratio), sufficient to form a two centimeter-thick polymer layer after curing, is poured into the dish. After curing, the foil assembly is easily released from the PDMS replica, and the replica is sandwiched between two partially cured flat pieces of PDMS and annealed to form a well-sealed channel. Finally, slight vacuum is applied during the annealing to remove air bubbles trapped between the flow channel module and the flat pieces, and the sealed separator 300 is then ready for use (preferably after the chip is rinsed with ethanol and with de-ionized water, and then dried with compressed nitrogen gas). A flat piece of PDMS which served as a cover to seal the chip by adhesion is also preferably cleaned and dried in the same manner.

It will be understood that the particular fabrication process described above is for purposes of illustration only. For example, the dimensions of membraneless separator 300 may be altered without departing from the scope of the present invention. Additionally, for example, it will be understood that the invention is not limited to the use of copper foil, and that other fabrication processes not described may also be employed.

Figure 4:
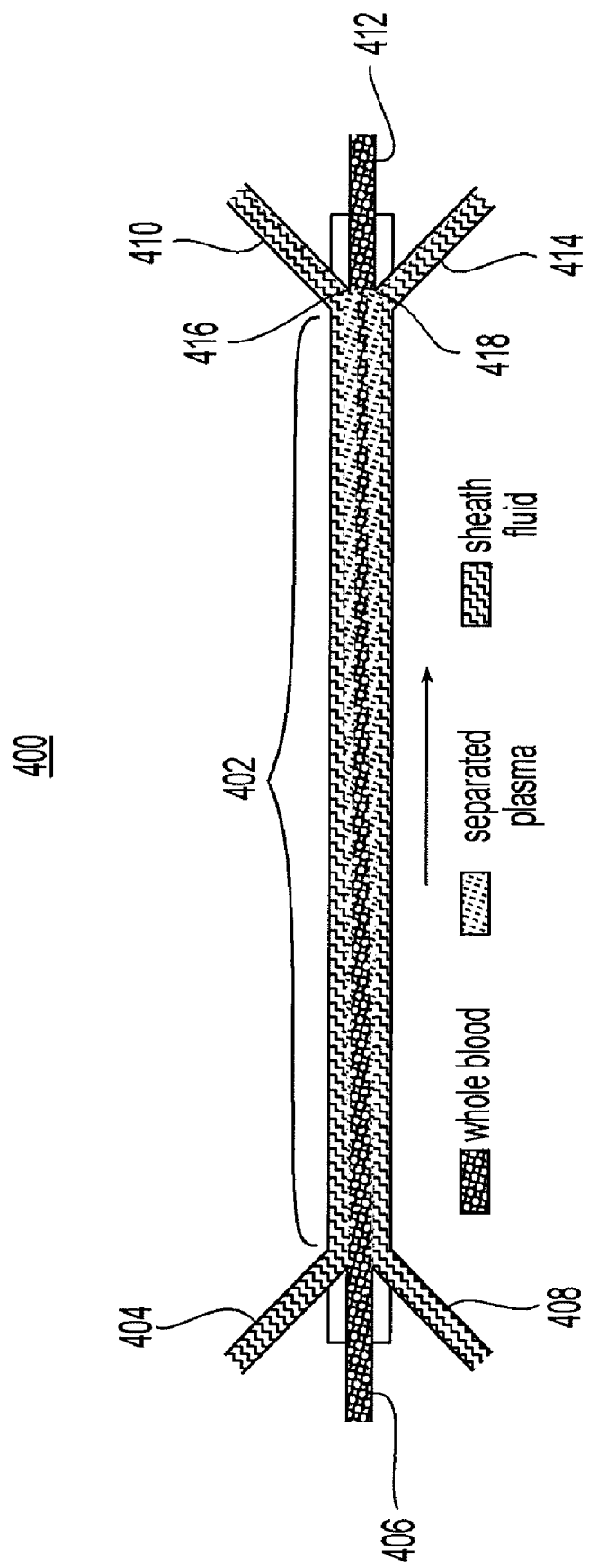
FIG. 4 shows membraneless separator used for the purpose of plasmapheresis in accordance with the principles of the present invention.

FIG. 4 shows a membraneless separator 400 according to the principles of the present invention. Similar to separator 300 described above, separator 400 includes an extraction channel 402, three separate inlet channels 404, 406 and 408 and three corresponding exit channels 410, 412 and 414. As also shown in FIG. 4, a first diverter 416 is formed from portions of exit channels 410 and 412, while a second diverter 418 is formed from portions of exit channels 412 and 414. It will be understood, however, that the invention is not limited by the number of exit channels (or inlet channels) that are used, nor is the invention limited by the number of diverters formed therefrom.

Figure 5:
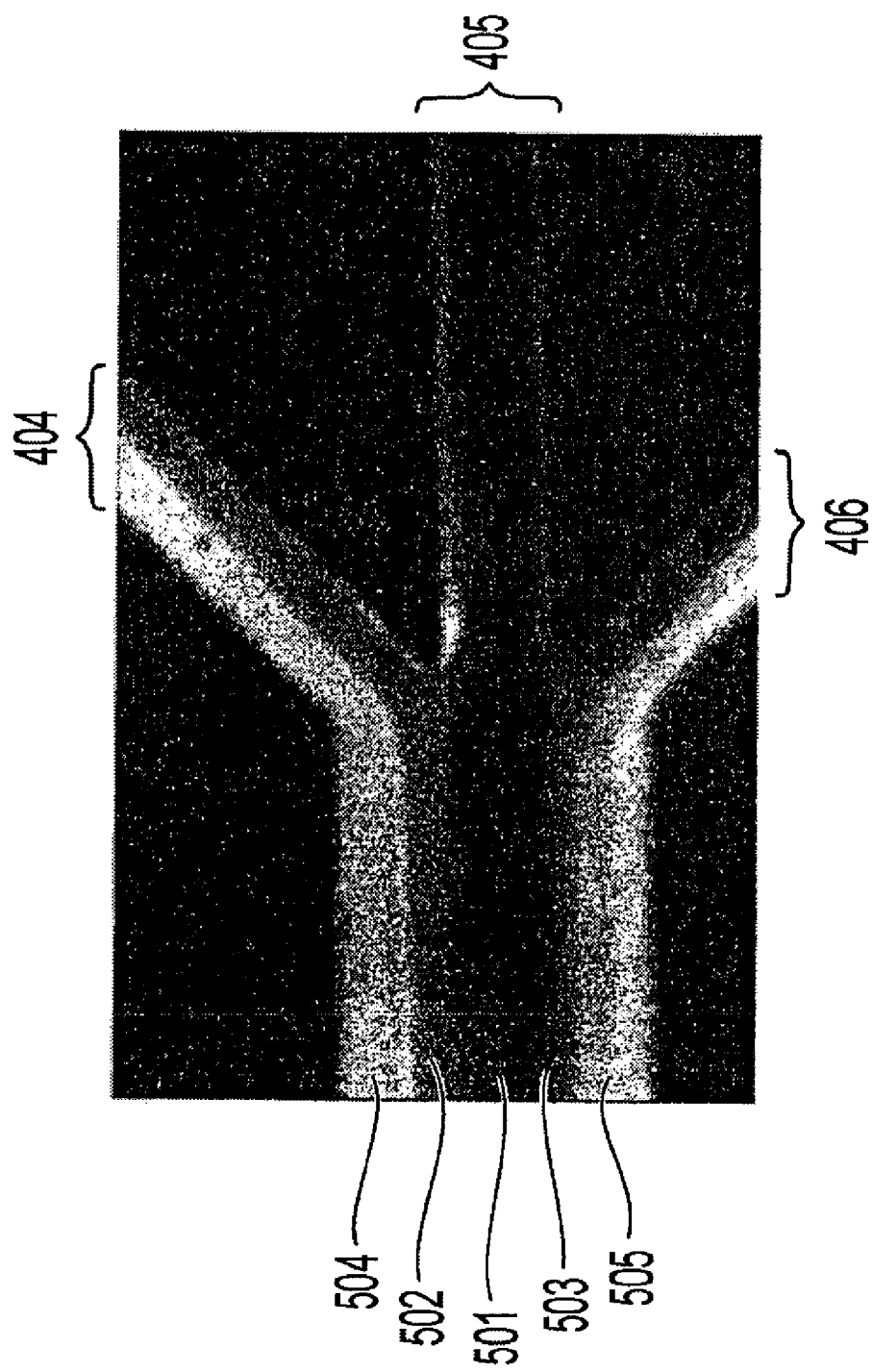
FIG. 5 shows the image of a portion of the membraneless separator of FIG. 5 while plasma is being skimmed from blood, as obtained by using a CCD camera.

As illustrated in FIG. 4, membraneless separator 400 can be used as a plasmapheresis device in accordance with the principles of the present invention. For example, as shown in FIG. 4, plasma from the blood entering extraction channel 402 through inlet channel 406 is skimmed and exits with sheath fluid through exit channels 410 and 414. This process of skimming is explained in greater detail below in connection with FIG. 7, FIG. 5, meanwhile, shows an image of the right-most portion of separator 400 shown in FIG. 4, as obtained by using a CCD camera (Sensys0401E, Roper Scientific). In particular, the image of FIG. 5 illustrates plasma being skimmed from blood according to the principles of the present invention. As shown in FIG. 5, a portion of the blood 501 provided through inlet channel 402 (not shown) exits through exit channel 405. Moreover, while cellular components of blood 501 migrate to the center (as explained below in connection with FIG. 7), cell-depleted (or cell-free) fractions of blood 501 such as plasma 502 and 503 combine with sheath fluid 504 and 505 to exit extraction channel 400 through exit channels 404 and 406, respectively.

It will be understood by persons skilled in the art that a membraneless separator as described herein is not intended to, nor could it, offer sufficient discrimination between the substances it is intended to remove and those it is intended to leave behind. Accordingly, for example, membraneless separators as described above will only function by themselves in the exceptional circumstance that all the components of plasma are to be removed. For example, a membraneless separator may be used alone when the removal of plasma, usually not in its entirety but without discrimination among its components, is to be removed, and the cellular components of blood are to be left behind.

Figure 6:
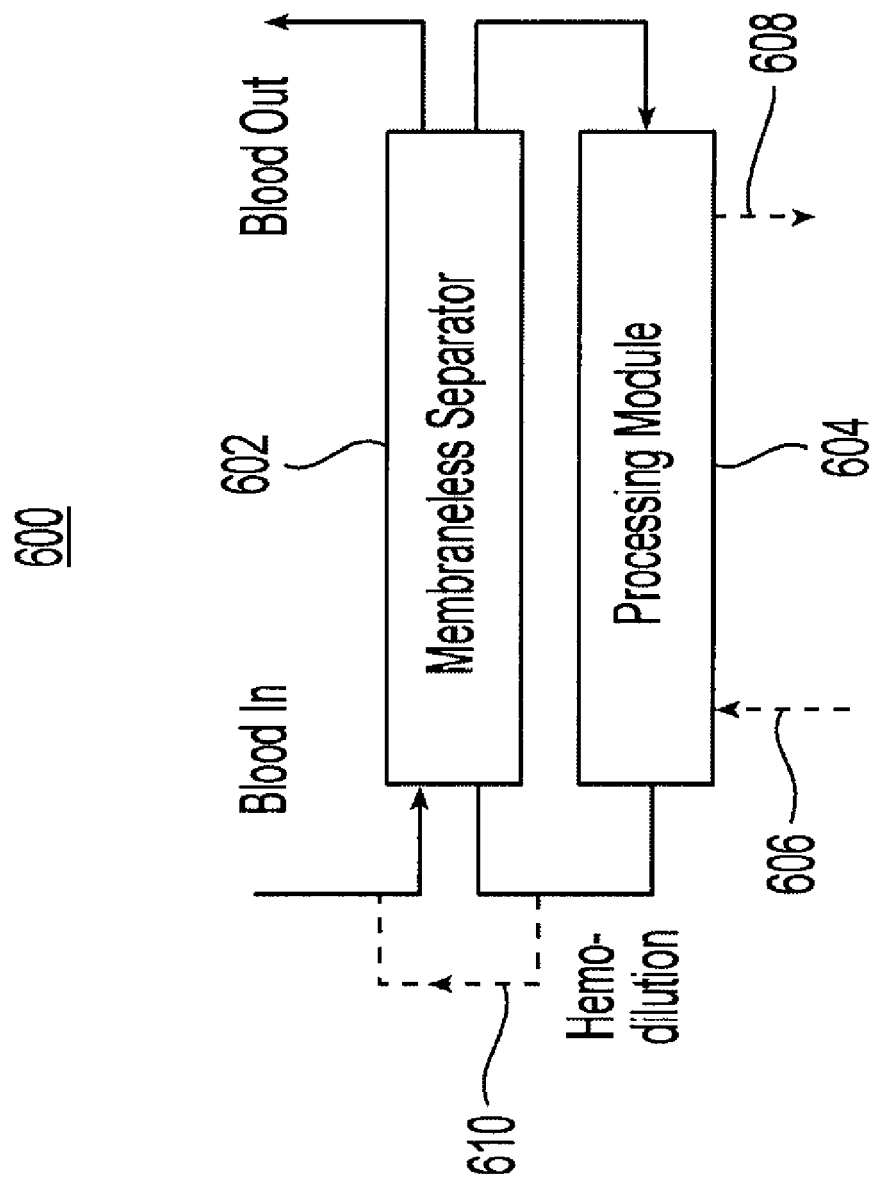
FIG. 6 shows a simplified block diagram of a system including a membraneless separator and a secondary separator in accordance with the principles of the present invention.

In all other circumstances, according to the principles of the present invention, a membraneless separator will operate in conjunction with a secondary separator that receives the sheath fluid and, optionally, a cell-depleted (or cell-free) part of the bloodstream. For example, to prevent the removal of macromolecules, the secondary separator can be used to generate a stream rich in macromolecules and free of small metabolite molecules and middle molecules that is recycled in sheath fluid to the membraneless separator. Thus, according to the invention, the secondary separator regulates the operation of the membraneless separator through the composition of the recycle stream that it returns to the inlets for sheath fluid of the membraneless separator (as shown in FIG. 6 and described in greater detail below). It should be understood that the secondary separator may incorporate a variety of means to remove solutes whose extraction removal from the circulation (i.e., the recycle stream) is desired, and that the invention is not limited in this manner.

One substance whose transport (i.e., removal from blood being processed) is typically undesirable is albumin. In each pass through an exchange device according to the invention, for example, albumin would be removed at more than ¼th the rate of small solutes, and albumin (which is confined to the blood space of an animal) would undergo perhaps 10 times as many passes as would urea which is distributed throughout the total body water reservoir. Thus, the fractional removal of albumin, even though its inherent diffusivity is smaller, would exceed the fractional removal of urea. According to the principles of the present invention, therefore, a secondary separator (e.g., a membrane device that permits extraction of urea and water but not albumin) may be used to recycle albumin to the blood. In particular, the sheath fluid received from the recycle stream will be depleted of urea and water, but will be rich in albumin. Thus, the composition of this stream will recruit the further extraction of urea and water but will not recruit further extraction of albumin, given that the difference in albumin concentration between the blood being processed and the sheath fluid will have disappeared.

It will be understood that an important specification of how the membraneless separator operates is the difference between the inlet flow rate and the outlet flow rate of the sheath fluid. For example, when these flows are equal and urea and water are removed by the secondary separator, there will be, at first, an insufficient transfer of water from blood to the sheath fluid to keep up with water removal in the secondary separator. Thus the concentration of proteins, including albumin, will rise in the recycle stream. When this concentration has reached a sufficiently high level, water transfer will be enhanced by a difference in protein osmotic (oncotic) pressure between the blood and the sheath fluid. Thus, the membraneless separator will balance its performance to that of the secondary separator. On the other hand, if the rate of withdrawal of sheath fluid is greater than its rate of supply, sufficient water may be sent to the secondary separator to keep up with its rate of water removal, but protein concentration will rise again until a concentration difference exists in the membraneless separator between the sheath fluid and the blood, causing a diffusion of protein back into the bloodstream. Once again, the membraneless separator will balance its performance to that of the secondary separator.

For example, when the principal goal of the treatment is the removal of highly diffusible (in general, low molecular weight) molecules, assuming a flow of 20 ml/min flow, the contact area in the membraneless separator will be in the range about 17 to 71 $cm^2$. When the principal goal of the treatment is the removal of slowly diffusible molecules (e.g., proteins and especially immunoglobulins), the contact area in the membraneless separator will be larger, in the range of approximately 1,700 to 7,100 $cm^2$ (assuming a flow of 20 ml/min), and the secondary separator will be configured to remove these molecules and to recycle smaller molecules (unless their simultaneous removal is desired).

FIG. 6 shows a simplified block diagram of a system 600 including membraneless separator 602 and secondary separator 604 in accordance with the principles of the present invention. Although not shown in detail, it will be understood that membraneless separator 602 may be similar to those separators shown in FIGS. 3 and 4 and described above, for example.

According to the principles of the present invention, blood that is to undergo processing is provided to (and removed from) membraneless separator 602. Meanwhile, sheathing fluid that is recycled by secondary separator 604 is also provided to (and removed from) membraneless separator 602. As also shown in FIG. 6, whenever secondary separator 604 transfers solutes to a second fluid (e.g., dialysate), fresh dialysate connection 606 and waste dialysate connection 608 may be used for providing fresh and waste dialysate streams, respectively. It will be understood that shunting of fresh fluid directly to the blood stream, as represented by dashed line 610, is also a possibility (but not mandatory). In general, FIG. 6 makes the role of membraneless separator 602 clear: to equilibrate solutes of interest with the sheathing fluid without transfer of cells.

It will be understood that secondary separator 604 may use any of many available separation principles known to those skilled in the art, including ultrafiltration and sorption using a wide range of sorbents targeted to particular small and large molecules, chemical reaction, and precipitation. Plasma diafiltration (a variant of hemodiafiltration), for example, may also be used according to the principles of the present invention. The following international publications which refer to hemodiafilters are incorporated by reference herein: WO 02/062454 (Application No. PCT/US02/03741), WO 02/45813 (Application No. PCT US01/47211), and WO 02/36246 (Application No. PCT/US01/45369). According to additional embodiments of the present invention, moreover, when low-molecular weight solutes are to be removed by plasma diafiltration, a stream of sterile buffer is added to the blood to allow a greater volume of fluid, with its accompanying small molecules, to pass through the diafiltration membrane. In conventional diafiltration, this volume may be added before or after the diafilter. In this invention, however, it is advantageous to add it either to the bloodstream or the recycle fluid from the secondary separator 604, which is the primary source of sheath fluid.

Figure 7:
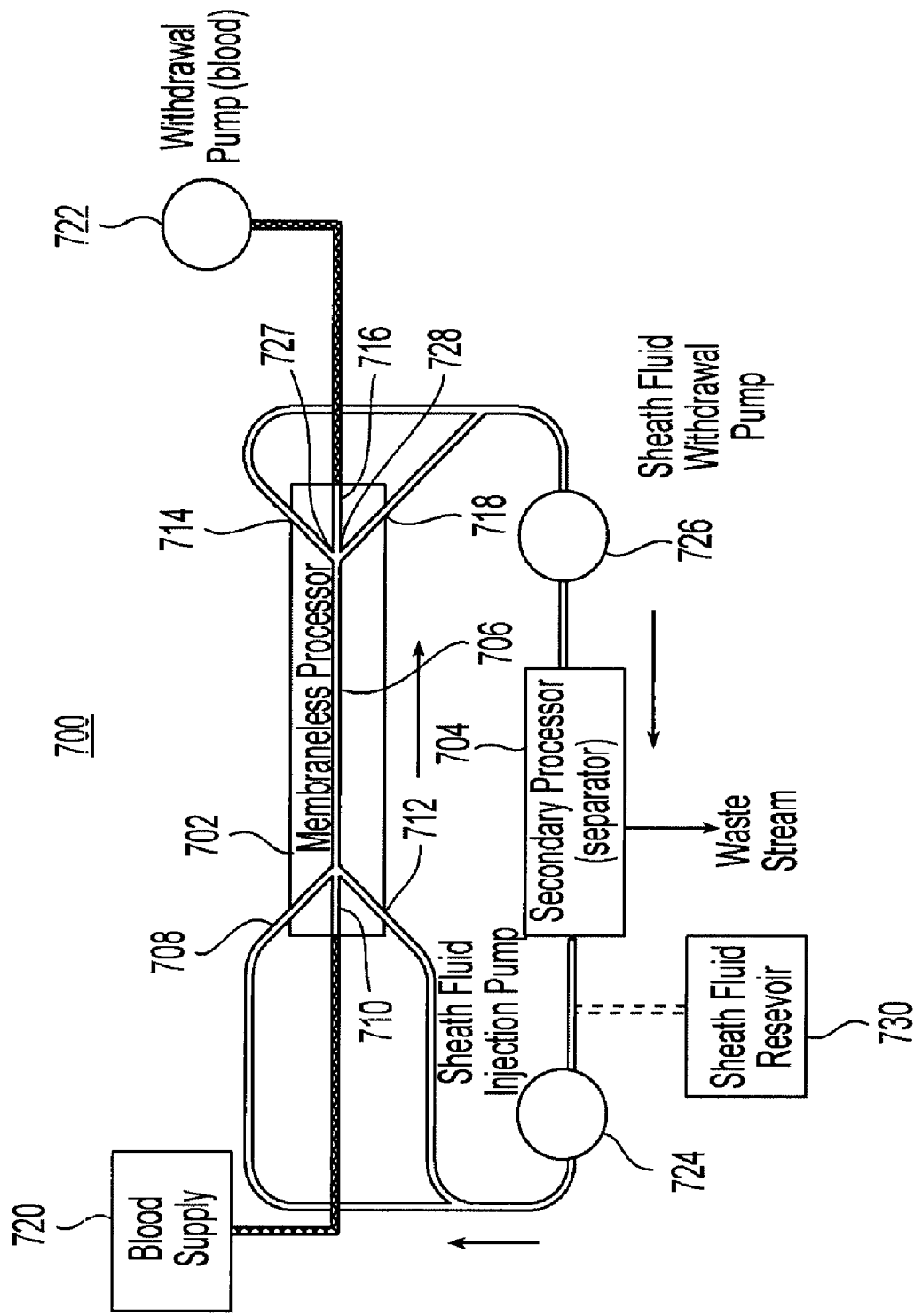
FIG. 7 shows a more detailed view of a system including primary and secondary separators in accordance with the principles of the present invention.

A more detailed view of a system 700 which includes membraneless separator 702 and secondary separator 704 in accordance with the principles of the present invention is shown in FIG. 7. As shown in FIG. 7, separator 702 includes extraction channel 706, inlet channels 708, 710 and 712 and exit channels 714, 716 and 718.

According to the principles of the present invention, system 700 also includes blood supply 720, and a plurality of pumps 722, 724 and 726 (which may be either manually or automatically operated, such as by using detection and regulation techniques described below). As shown in FIG. 7, blood supply 720 provides blood to be processed to membraneless separator 702 through blood inlet channel 710. It will be understood that blood supply 720 may be a living person or other animal, for example, or may be a blood reservoir. Blood withdrawal pump 722, meanwhile, is responsible for removing blood from separator 702 through blood exit channel 716.

As illustrated by FIG. 7, the flow of sheath fluid (or extractor fluid) into separator 702, through sheath inlet channels 708 and 712, is controlled by sheath fluid injection pump 724 (which preferably provides sheath fluid in equal parts to channels 708 and 712). The flow of sheath fluid out of separator 702, through sheath exit channels 714 and 718, meanwhile, is controlled by sheath fluid withdrawal pump 726 (which preferably draws equal amounts of sheath fluid out of channels 714 and 718). According to preferred embodiments of the present invention, pump 724 is a two-chamber pump that provides sheath fluid at equal velocities (and with substantially similar composition) to both inlet channels 708 and 712, while pump 726 is a two-chamber pump that removes sheath fluid from exit channels 714 and 718 at equal velocities. Moreover, it is also contemplated that pump 724 be replaced by two pumps (not shown) for separately providing sheath fluid to inlet channels 708 and 712, in which case the composition of the sheath fluid entering inlet channel 708 may be substantially similar to, or different from, the sheath fluid entering inlet channel 712. Similarly, two pumps (not shown) can be used in place of pump 726 for the purpose of separately withdrawing sheath fluid from exit channels 714 and 718. It is also contemplated that, in other embodiments of the present invention, sheath fluid entering through inlet channel 708 and exiting through exit channel 714 flows at a different velocity than the sheath fluid entering through inlet channel 712 and exiting through exit channel 718. It will be understood that the invention is not limited by the particular usage of pumps or sheath velocities described herein in connection with the description of FIG. 7.

As explained above, a membraneless separator according to the invention also needs one or more diverters to operate. Thus, according to the principles of the present invention, a first diverter 727 is formed from a portion of sheath exit channel 714 and a portion of blood exit channel 716. Moreover, a second diverter 728 is formed using a portion of blood exit channel 716 and a portion of sheath exit channel 718. It will be understood that, in embodiments of the present invention using more than two layers of sheath fluid, addition diverters will be used.

In certain preferred embodiments of the invention, the sheath fluid provided to separator 702 (from separator 704 and/or optional sheath fluid reservoir 730) by sheath fluid injection pump 724 occupies approximately $\frac{2}{3}$ of the cross-section of extraction channel 706, with blood from blood supply 720 in the middle $\frac{1}{3}$. In this manner, each half of the blood layer in extraction channel 706 is "serviced" by one of the sheathing layers, and the sheathing layers are traveling at an average velocity that is approximately half that of the blood (even though the interfacial velocities of the blood and sheathing fluids are equal). Thus, the volume of blood and the volume of sheathing fluid that pass through the unit in a given period of time are approximately equal. Although the invention is not limited in this manner, it should be noted that, in the configurations described here, efficiency drops when the volumetric flows of the two fluids (i.e., blood and sheath fluid) are very different from each other.

In order to cause the separation (or skimming) of all or part of the cell-depleted component of the blood being processed, according to various embodiments of the present invention, the inlet and exit flows of the sheath fluid are controlled (via pumps 724 and 726, respectively) such that more sheath fluid is withdrawn from separator 702 than is provided thereto. For example, it is possible to skim 10% of the blood flow by running sheath fluid withdrawal pump 726 at a rate that is 10% higher than the rate of sheath fluid injection pump 724. It will be appreciated that, when this is done, the blood efflux rate is determined and need not be controlled, as it should naturally have an outflow that is 90% of the inflow.

As explained above, when indiscriminate plasma removal is not desired, the plasma that is skimmed from the blood using membraneless separator 702 is processed by secondary separator 704, which regulates the operation of separator 702 through the composition of the recycle stream that it returns to sheath inlets channels 708 and 712 (i.e., a recycle stream is used to limit transport of blood components for which extraction is not desirable). According to the principles of the present invention, a substantial benefit arises because secondary separator 704, whether membraneless or not, is able to achieve high filtration velocities due to the fact that concentration polarization is limited to proteins and does not involve cells. Moreover, because cells are retained in the membraneless separator 702, they would see artificial material only on its conduit surfaces, not on its liquid-liquid contact area, with the result being a reduction in bioincompatibilities and a reduced (or eliminated) need for anticoagulation. Additionally, because the primary transport surface in the system is intrinsically non-fouling, a major deterrent to long-term or continuous operation is removed, opening the possibility of a wearable system with the recognized benefits of prolonged, slow exchange.

It should be understood that any operation of membraneless separator 702 that allows the sheath exit flows to be larger than the corresponding inlet values will induce a convective flow from the blood stream, over and above the diffusive flow. In order to prevent such a convective flow from carrying blood cells with it (as would be the case if the distribution of cells in the blood stream was uniform), it is important that cellular components of the blood have migrated to the center of the blood stream in order to permit significant plasma skimming. As should be appreciated by those skilled in the art, centripetal drift of cells occurs under a variety of flow regimes. According to the invention, therefore, various flow conditions can be used that cause blood cells to move away from the blood-liquid interface. For example, when blood flows in a tube below a wall shear rate (measured as the blood-flow velocity gradient perpendicular to the tube wall) of about 100 reciprocal seconds, this shear rate causes cellular components to migrate the center and leave the sheath as cell-free, essentially pure plasma. (See Goldsmith, H. L. and Spain, S., Margination of leukocytes in blood flow through small tubes, Microvasc. Res. 1984 March; 27(2):204-22.)

It will be appreciated that long-term stability is necessary for satisfactory operation of the microfluidic devices described herein. For example, it is desirable to prevent inappropriate splitting of an exit stream which, uncorrected, could result either in loss of cells or unintended infusion of sheathing solution into the bloodstream. Moreover, the presence of blood cells in the sheath, or extractor fluid may also be undesirable. According to another aspect of the present invention, therefore, on-board electronics and photonics (not shown), which are common features of chip-based microfluidic devices, may be used. In particular, such electronics or photonics could be used to regulate system 700 (i.e., to introduce flow changes) with an electrically activated device (e.g., a piezoelectric valve) that is mounted on the same plate, or "chip," on which separator 702 is located.

According to one embodiment of the invention, for example, very low concentrations of cells would be permitted and monitored (e.g., before or after the sheath fluid being provided to secondary separator 704) by using any suitable detector, such as a photo detector. An ultramicroscope (a light-scattering device that is particularly sensitive to the presence of dilute particles) is one example of a photo detector which can be used. Based on this monitoring, flow corrections that would provide the system with long-term stability can be made which include, for example, adjusting the blood-sheath fluid interface. In particular, by adjusting the flows to separator 702 to reposition the interface, desired components can be retained in the blood. For example, when an excessive number of blood cells is present, the flow of blood could be decreased (or the flow of extractor fluid increased) in order to shift the blood-sheath fluid interface accordingly.

Additionally, according to another aspect of the invention, on-board electronics can be used to protect against the type of flow imbalances that might cause large blood losses in one direction or massive hypervolemia in the other direction, which are naturally prevented when a membrane is present but which may occur in a membraneless device. It will be understood by those skilled in the art this type of detection and regulation may also be used with in conjunction with the other embodiments of the present invention described above.

As explained above, in all membraneless contact configurations, the fluids (e.g., blood and sheath fluid) must flow in the same direction. In particular, any flow in opposite directions would disrupt the blood-fluid interface and induce undesirable advection. Moreover, since the fluids must flow in the same direction, the most that can be accomplished in one membraneless unit according to the invention is the equilibration of the sheath and blood streams (which, according to Loschmidt's formula provided above, means that if the sheathing fluid is flowed at the same rate as blood, the extraction E of a solute cannot exceed ½). In other words, if the two flows are equal, at most half of any solute can be transferred. Moreover, while greater flows permit larger fractions, E, of a solute to be removed, they require higher circulation rates to the secondary separator and thus force processing of solutes at lower concentrations, which is generally undesirable. Therefore, it is generally desirable for these flows to be nearly equal, within at least a factor of 2 or 3.

This limitation on extraction can be largely overcome, however, by the configurations shown in FIGS. 8 and 9 and described below which achieve the effect of opposing flows (counterflow) by the juxtapositions of modules. In particular, low extraction efficiency can be overcome by more sophisticated layouts of a microfluidic system such that flows are concurrent in each unit of the system, but the overall flow approaches countercurrency in pattern and efficiency.

According to the invention, subdivision of a given, desired contact area into n units each connected to the other in a countercurrent manner, even though the flow within them is concurrent, is used to allow extraction efficiency to rise according to the formula provided above. Thus, if an area were divided into four units, for example, and each had an extraction efficiency of 50%, the composite unit would have an efficiency of 0.8 or 80%.

Figure 8:
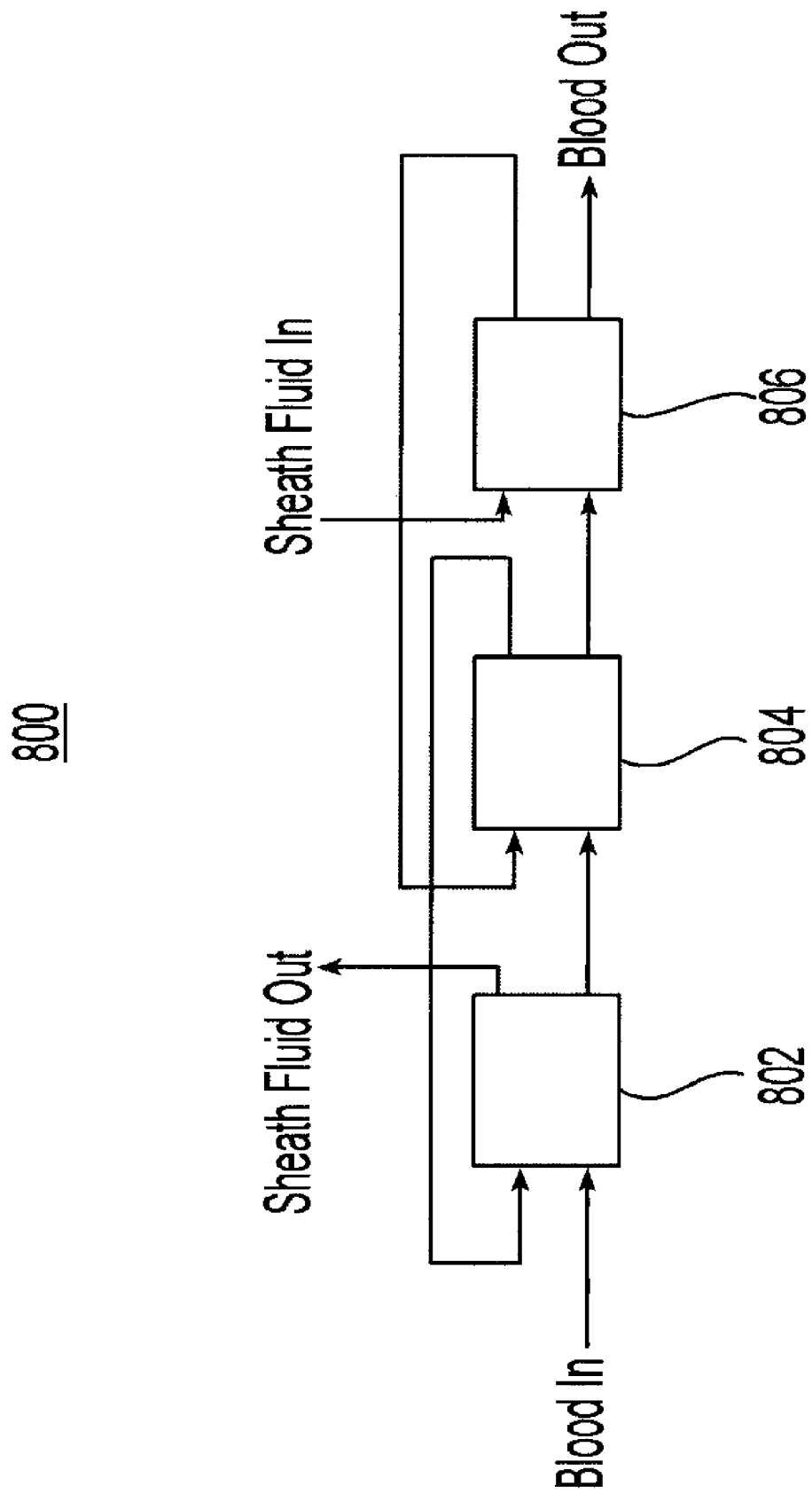
FIG. 8 shows the configuration of a system subdivided into three units in accordance with the principles of the present invention.

FIG. 8 shows the configuration of a system 800 according to the invention in which the total area of contact is partitioned into three sub-units 802, 804 and 806 (i.e., n=3). In operation, blood to be processed is first provided to sub-unit 802, then passes through sub-unit 804, and finally, exits out of sub-unit 806. The sheath fluid to be used in system 800, on the other hand, is first provided to sub-unit 806 (at this point, the sheath fluid has no blood components). The sheath fluid exiting sub-unit 806 is next provided to sub-unit 804, and after exiting sub-unit 804, is provided to sub-unit 802. Thus, assuming each unit has an extraction efficiency of 50%, the overall extraction efficiency of the composite unit, $E_O$, is equal to 0.75 or 75%. Accordingly, it becomes possible, at equal flows, to remove 75% rather than only 50% of the solute of interest. In will be understood that the extraction efficiency approaches 1.0 or 100% as the number of small units approaches infinity. Persons skilled in the art will appreciate that, although not shown, the sheath fluid exiting sub-unit 802 may be provided to a secondary separator as described above. Moreover, while three sub-units 802, 804 and 806 are shown in FIG. 8, it will be understood that any number of sub-units (e.g., 2, 4, 5, etc.) may be used in system 800, all of which may be easily introduced on a master chip fabricated according to well known techniques for the general fabrication of microfluidic devices.

Figure 9:
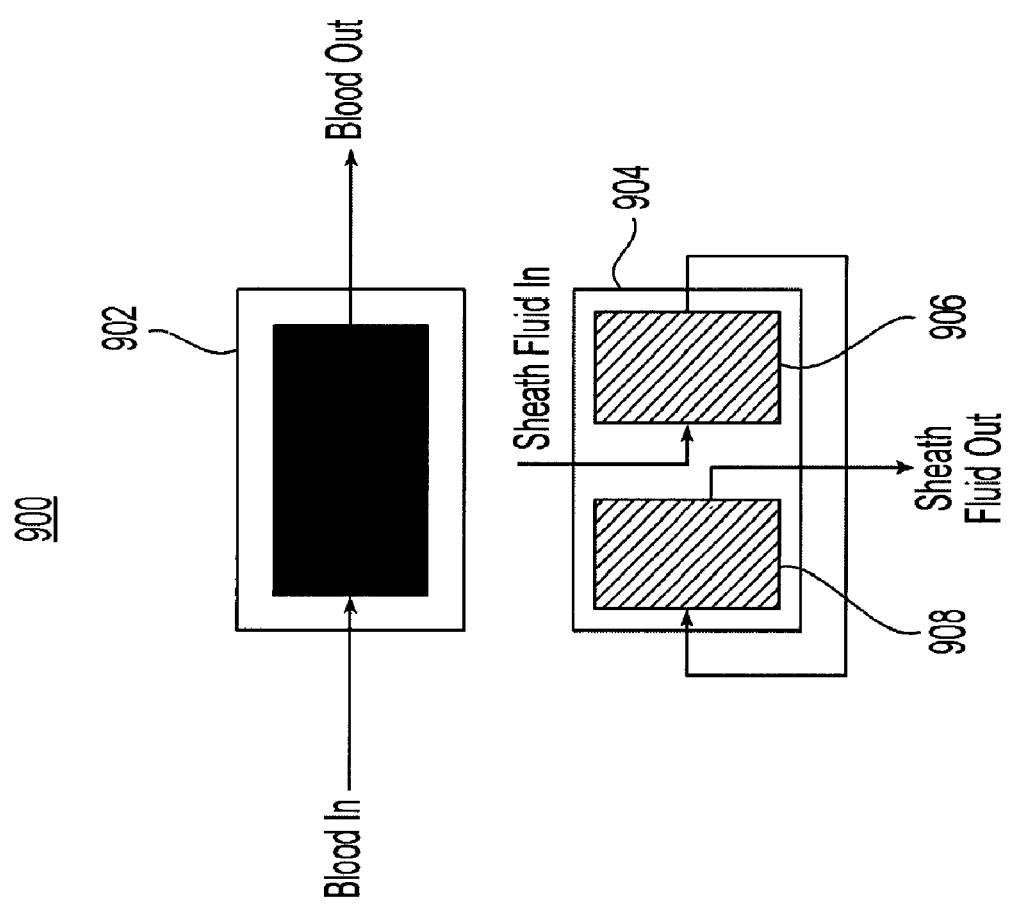
FIG. 9 shows the routing of fluids between separate units in accordance with the principles of the present invention.

FIG. 9 shows another example of a system 900 using sub-units according to the principles of the present invention. In particular, FIG. 9 shows two flow patterns 902 and 904 that would be superimposed on each other in a single cartridge. For example, the top could represent blood, while the bottom could represent an extractor fluid (e.g., dialysate). As shown in FIG. 9, sheath fluid flows through sub-unit 906 prior to flowing through sub-unit 908. In this manner, with sufficient contact area, the fraction of material in the blood layer that is extracted will be equal to ⅔ or 67%.

Persons skilled in the art will appreciate that many different fabrication techniques can be used in accordance with the principles of the present invention. In recent years, controlled fluid movement and transport among fluids has been achieved in very small channels and at very low rates of flow largely for the purpose of assaying the contents of a minute fluid sample in order to determine, for example, the catabolite concentration in the blood. These devices have been enabled by recently developed microfabrication methodologies. The Holy Grail has been the development of a "Lab on a Chip," in which several sequential analytical processes are conducted on a single chip that may be, for example, one square centimeter in area. Transport of a chemical or biochemical sample from one process to another and on and off the chip itself requires fluid handling capabilities, and thus, this enabling technology is commonly called "microfluidics." Microfluidics is essential for nearly all on-chip applications. The synthesis of chemicals in microfluidic geometries is an application that is perhaps closer in concept to the scope of this disclosure because of the need to process a relatively larger amount of fluid. Synthesis includes, perforce, the separations needed between the steps of a chemical reaction sequence. While the aims of synthesizers differ from ours, and embrace some issues that we do not now see as pertinent, all of this work, reported and emergent, is of interest. Specifically, the present invention embraces some of the fabrication techniques and experimental methods developed for the fabrication and characterization of microfluidic device structures, to define upwardly scalable transport to and from blood.

According to the invention, moreover, microchannel structures for flow experiments may be formed by a rapid-prototyping technique. For example, the required structures may be realized in PDMS (silicone) resin by replica-molding from master structures created in thick negative photo resist (SU-8) by optical lithography. Commercially available, standard grade mixtures of EPON SU-8 photo resist, SU-8-5 (52% solids), SU-8-25 (63% solids), SU-8 50 (69% solids) and SU-8 100 (73% solids), for example, may be spun onto Si wafer substrates at a speed of rotation that depended on the film thickness needed, yielding films that were 10 to 300 μm thick. For example, SU-8 50 spun at 1100 rpm yields a 100 μm film. Prior to exposure, moreover, the spun layer is preferably baked on a precisely leveled hot plate at 95° C. for a time that is dictated by the film thickness (ranging from minutes to hours). These samples are then allowed to cool before further processing. Post-bake exposure, meanwhile, can be done using a direct laser writing system. The photolithographic setup consists of an Ar-ion laser (wavelength λ350 nm), focusing optics, and a computer controlled sample stage. The movement of the stage along all three axes (x, y, z) is achieved by stepping motors. Desired master patterns were created by translating the samples underneath the focused laser beam to expose the outline, and then scanning across the interior so that the intended micro channel was fully exposed. Dynamical focus correction or the sample tilt with respect to the scanning laser beam was the done by on-the-fly adjustments of the distance between the focusing lens and the sample stage. In a preferred embodiment, this exposure is carried out at 95° C. for 15 min. Development, meanwhile, can be carried out in a commercial SU8 developer, again for a time based on film thickness (with the sample being lightly stirred during development). Patterns created in SU-8, meanwhile, are used as molding masters for replication in PDMS. PDMS is prepared from a mixture of PDMS precursor and curing agent (Sylgard 184 kit, Dow Corning) in a 10:1 ratio by weight. Before curing, the mixture is placed in vacuum to evacuate bubbles formed during mixing. It is then poured over the SU-8 master, which had been previously coated with a thin layer (~50 nm) of chromium to improve the release of the PDMS casting, after curing. Curing is done at 70° C. for approximately twelve hours. Once the SU-8 film is spun, pre-baked and cooled as described above, a Karl Zeiss MJP3P Contact Mask Aligner can be used for exposure, together with standard chromium masks or transparency masks depending on the resolution required. The films are then post-baked, and developed in the manner outlined in the previous section. The same pattern transfer technique is used to produce PDMS replicas.

It is apparent to those skilled in the art that many advantages may be provided in the various embodiments of the present invention described above. For example, the devices, systems and methods according to the principles of the present invention are capable of diffusing various blood components having different sizes, including 'small' molecules, 'middle' molecules, macromolecules, macromolecular aggregates, and cells, from a blood sample to the extractor fluid. This ability is particularly important considering the fact that different treatments require the removal of different sized particles. For example, in dialysis, one may desire to remove molecules of low molecular weight, while in the treatment of acute liver failure, both small and intermediate-sized molecules are to be removed. In therapeutic apheresis, meanwhile, one generally wishes to remove selected protein macromolecules (e.g., immunoglobulins), while in the treatments for fulminating sepsis, it is toxins of intermediate molecular weight that one generally desires to remove. On the other hand, in proposed anti-viral treatments, one wishes to remove free viral particles, while in the treatment of congestive heart failure, one simply wishes to remove water.

It should also be apparent that a device or system according to the invention may be used to process the blood of a single individual for the purpose of treating any of a large number of disease states. For example, therapies according to the invention may be used in the treatment of acute renal failure, acute liver failure, high antibody levels in myasthenia gravis and other autoimmune diseases. Additional uses include, for example, the removal by either precipitation or sorption of LDL in homozygous hyperlipidemia, in addition to the removal of malignant sepsis or fluid in cases of congestive heart failure, for example. The invention may also be used to aid in the reduction of viral burdens in AIDS patients, as well as for treatment of patients requiring other types of blood purification. Patients with diabetes, patients that have suffered a drug overdose, patients that have ingested a poison, patients suffering from renal failure, patients suffering from acute or chronic liver failure, or patients that have Myasthenia gravis, lupus erythematosis, or another autoimmune disease may also benefit from the devices and systems of the present invention. For example, while an exchange device according to the invention is not a cure for diabetes, it can be useful in the amelioration one or more symptoms of diabetes. Moreover, the device or system of the invention could be useful in clearing the blood of IgG molecules or other molecules, which are causative of an autoimmunity disorder. Additionally, the device or system of the invention can be used in acute dialysis or for extended dialysis. One skilled in the art will also appreciate that patients (or animals, in the case of veterinary use of the present invention) suffering from disorders, diseases and syndromes not listed herein may nonetheless be included in the patient pool intended for the device and system according to the invention.

Additionally, because the membraneless devices and systems described above have a small need for supporting machinery, and may be expected to be much smaller, to avoid high cell concentrations and membrane contact, and to operate throughout at low rates of shear, they are especially compatible with cognate processes. In one embodiment, a wearable (or at least portable) system according to the invention can run between 20 and 24 hours per day at a flow rate of about 20 cc/min, for example. The patient could then have, for example, 4-5 hours each day without the device in place which could be used for personal hygiene (e.g., showers or baths), sports activities, or other activities not amenable to the small system being worn or used. The invention thus addresses a problem recognized by the dialysis community (i.e., the negative side effects such as physical exhaustion, thirst, etc. associated with an episodic dialysis schedule), for which daily or nocturnal hemodialysis is not always a sufficient alternative. In particular, the invention described herein allows the patient to move about in a normal manner (e.g., go to work, school, home, etc.) while being subject to ongoing dialysis.

In addition to the treatment of various disease states, a device or system according to the invention may also be used for extracting blood components that are useful in treating others, as well as for purposes of studying the processes by which molecules and cells segregate and diffuse in blood. For example, it is known to those skilled in the art that diffusion of individual molecular species in blood may not occur independently and may not depend on size in the simple manner dictated by the Stokes-Einstein equation. Moreover, many solutes may partition into multiple forms: free, in complexes, bound to plasma protein, bound to cell-surface moieties, or as intracellular solutes. Relative to the rate of diffusion of the solute, its different forms may or may not be in local equilibrium. These phenomena are likely obscured when a membrane is present because it slows and controls overall transfer rates. Therefore, a membraneless device or system according to the invention can be a useful scientific tool to study these phenomena and a system in which rates are raised enough that partitioning may set limits on how much and how quickly a solute can be removed. A particular example is bilirubin bound to albumin. Another example is inorganic phosphorous which exists as partially ionized salts, as two anionic forms in plasma and in several intracellular forms.

Persons skilled in the art will also appreciate that the present invention can be practiced by other than the described embodiments, which are presented for purposes of illustration and not of limitation, and that the present invention is limited only by the claims that follow.

The invention claimed is:

1. A method of performing a blood treatment, comprising:
along a microfluidic channel, placing blood from a patient in direct contact with an extraction fluid, without mixing, such that blood proteins and uremic toxins move from the blood into the extraction fluid;
moving the extraction fluid out of contact with the blood at an end of the channel and into contact with a membrane at a pressure, and thereby passing water and uremic toxins in the extraction fluid through the membrane at a pressure sufficient to concentrate the blood proteins in a fraction of the extraction fluid and placing the resulting fraction in direct contact with the blood at a beginning of the channel, a recirculation of extraction fluid resulting in a concentration of blood proteins such that blood proteins are returned to the blood in the channel by diffusion.

2. The method of claim 1, wherein the placing includes preventing cells from moving from the blood into the extraction fluid.

3. The method of claim 1, wherein the placing includes flowing the blood and extraction fluid through the microfluidic channel, the channel having a ratio of width (the dimension perpendicular to flow direction and parallel to the interface between the blood and extraction fluid) and height (the direction normal to the interface between the blood and extraction fluid) that is more than 10.

4. The method of claim 3, wherein the placing includes flowing the blood and extraction fluid through the microfluidic channel, which has a ratio of width to height that is more than 50.

5. The method of claim 3, wherein the channel height is less than 100 microns.

6. The method of claim 1, wherein the extraction fluid includes dialysate.

7. The method of claim 6, wherein the placing includes creating a laminar flow of the blood and extraction fluids including two layers of extraction fluid with a blood layer sandwiched between them.

8. The method of claim 1, wherein the placing includes creating a laminar flow of the blood and extraction fluids.

9. The method of claim 1, wherein the placing includes creating a laminar flow of the blood and extraction fluids including two layers of extraction fluid with a blood layer sandwiched between them;
the flow being created in the microfluidic channel, which has a ratio of width (the dimension perpendicular to flow direction and parallel to the interface between the blood and extraction fluid) to height (the direction normal to the interface between the blood and extraction fluid) of more than 10 and has a height of less than 100 microns.

10. The method of claim 1, wherein the placing includes creating a laminar parallel flow of the blood and extraction fluids including two layers of extraction fluid with a blood layer sandwiched between them, the total volume flow rate of blood and the total volume flow rate of extraction fluid being approximately the same.

11. The method of claim 1, wherein the placing includes creating a laminar flow of the blood and extraction fluids including two layers of extraction fluid and a blood layer sandwiched between them, the total volume flow rate of blood in the blood layer and the total volume flow rate of extraction fluid in the two extraction fluid layers being approximately the same.

12. The method of claim 1, wherein the passing includes circulating the extraction fluid across a single side of the membrane without passing it through the membrane such that the resulting fraction is depleted of water and uremic toxins.

13. The method of claim 1, wherein the placing includes pumping the extraction fluid using a first pump and pumping the blood using a second pump.

14. The method of claim 1, wherein the placing includes flowing the blood and extraction fluid to form a flat blood layer such that blood cells tend to drift toward a center of the blood layer.

15. The method of claim 1, wherein the placing includes flowing the blood and extraction fluid to form a flat blood layer and at least one extraction fluid layer, the combined blood layer and at least one extraction fluid layer defining a velocity profile in which the blood layer coincides with a region of minimum shear rate such that cells tend to remain in the blood layer as a result of a tendency of cells to migrate away from high shear rate regions of a flow.

16. The method of claim 1, wherein the placing includes creating a laminar parallel flow between walls of the microfluidic channel that includes two layers of extraction fluid with a blood layer sandwiched between them, the flow being such that the cells within the blood layer do not contact the walls.

17. A method of performing a blood treatment, comprising:
establishing a flow of blood and extraction fluid in a channel such that the blood and extraction fluid are in direct contact and such that entering and exiting flows of each of the blood and extraction fluid into and from the channel are established, respectively, at opposing ends of the channel, the exiting flow of extraction fluid containing blood proteins diffused there into;
conveying a portion of the extraction fluid in the extraction fluid exiting flow to the extraction fluid entering flow and further passing the extraction fluid portion across a membrane at a pressure such as to expel water and uremic toxins therethrough; and
permitting proteins to concentrate in the extraction fluid such that a quantity of the blood proteins leaving the channel in the extraction fluid exiting flow is substantially equal to the quantity of the blood proteins returned to the channel entering flow.

18. The method of claim 17, wherein the establishing includes retaining blood cells in the blood exiting flow and preventing them from leaving in the extraction fluid exiting flow by maintaining a lower shear rate at a location of the channel coinciding with the blood exiting flow than a shear rate at one or more locations of the channel coinciding with the extraction fluid exiting flow.

19. A method of performing a blood treatment, comprising:
flowing blood and dialysate into a microfluidic channel such that the blood and dialysate are in direct contact but remain in separate layers in the channel;
the flowing being such that a lower shear rate is maintained in the blood layer than a shear rate maintained in one or more dialysate layers, the difference in shear rate being sufficient to cause blood cells to be retained in the blood layer while permitting blood proteins and uremic toxins to diffuse into the one or more dialysate layers;
passing dialysate exiting the channel across one side of a membrane at a pressure such that water and uremic toxins flow through the membrane and out of the dialysate while preventing blood proteins from passing through the membrane thereby retaining the blood proteins in the dialysate such that the blood proteins concentrate in the dialysate and thereafter returning the dialysate and blood proteins back to the channel such that blood proteins are returned to the blood in the channel.

20. A method of performing a blood treatment, comprising:
passing, through a channel, blood from a patient and an extraction fluid, such that the blood and extraction fluid are in direct contact without mixing, the channel being configured such that substantial quantities of albumin and uremic toxins move from the blood into the extraction fluid;
placing the extraction fluid in contact with a membrane under pressure and, as a result, passing water and uremic toxins in the extraction fluid through the membrane;
placing processed extraction fluid in direct contact with blood; and
permitting the albumin to concentrate in the extraction fluid such that the substantial quantities of albumin are returned to the blood in the placing, wherein the flow of blood and extraction fluid in the channel during the passing, and the configuration of the channel, are such that blood is isolated from the channel walls by the extraction fluid and such that upon exiting the channel, a quantity of urea in the blood is substantially the same as a quantity of urea in the extraction fluid.

21. The method of claim 20, wherein the placing processed extraction fluid in direct contact with blood includes passing the processed extraction fluid through the channel.

22. The method of claim 20, wherein the placing processed extraction fluid in direct contact with blood includes passing the processed extraction fluid through the channel and the secondary treatment device is a membrane and the passing therethrough is effective to concentrate the albumin in a fraction of the extraction fluid.

23. A method of performing a blood treatment, comprising:
passing, through a channel, blood from a patient and an extraction fluid such that the blood and extraction fluid are in direct contact, the channel being configured such that substantial quantities of albumin and uremic toxins move from the blood into the extraction fluid;
removing the extraction fluid from the channel and flowing the extraction fluid on a side of a membrane, while providing a transmembrane pressure, and thereby passing water and uremic toxins in the extraction fluid through the membrane to concentrate the albumin in a fraction of the extraction fluid and returning at least a portion of the fraction back to the channel to be passed again therethrough in direct contact with blood, such that albumin is concentrated in the blood and thereby returned to the blood, wherein the flow of blood and extraction fluid in the channel during the passing and the configuration of the channel are such that blood is isolated from the channel walls by the extraction fluid and such that, upon exiting the channel, a quantity of urea in the blood is substantially the same as a quantity of urea in the extraction fluid.

24. A method of performing a blood treatment, comprising:
placing blood and an extraction fluid in non-mixing direct contact to produce a resulting extraction fluid containing non-cellular components, including albumin, transferred from the blood into the second extraction fluid;
removing the resulting extraction fluid from contact with the blood;
subjecting the resulting extraction fluid to a medical process including flowing the resulting extraction fluid alone a membrane with a transmembrane pressure sufficient to ultrafilter the resulting extraction fluid such that albumin is concentrated therein; and
placing the ultrafiltered extraction fluid back in direct contact with the blood such that at least the albumin is returned to the blood by diffusion resulting from the concentration of the at least the albumin in the ultrafiltered extraction fluid.

25. The method of claim 24, wherein the concentration of albumin in the extraction fluid is permitted to increase to the point where it is approximately the same as a concentration of albumin in the blood.

26. The method of claim 24, wherein the placing the blood and an extraction fluid includes flowing the blood and the extraction fluid in a microfluidic channel.

* * * * *

UNITED STATES PATENT AND TRADEMARK OFFICE
CERTIFICATE OF CORRECTION

PATENT NO.      : 7,588,550 B2
APPLICATION NO. : 11/776360
DATED           : September 15, 2009
INVENTOR(S)     : Edward F. Leonard et al.

It is certified that error appears in the above-identified patent and that said Letters Patent is hereby corrected as shown below:

On the title page:

Line (75) Inventors: Edward F. Leonard, ~~Scarsdale~~, NY
(US); Alan C. West, Tenafly, NJ (US);
Nina C. ~~Shaplely~~, New York, NY (US);
Zhongliang Tang, San Diego, CA (US) should read Line (75) Inventors: Edward F. Leonard, <u>Bronxville</u>, NY
(US); Alan C. West, Tenafly, NJ (US);
Nina C. <u>Shapley</u>, New York, NY (US);
Zhongliang Tang, San Diego, CA (US)

On the title page:

Please change "Dailysate" in the Figure to read --Dialysate--.

On sheet 1 of 9:

Please change "Dailysate" in FIG. 1 to read --Dialysate--.

Column 1, lines 19-20, please change "blood fluid)" to read --(e.g., blood fluid)--.

Column 3, lines 21-22, please change "is provides" to read --is provided--.

Column 6, line 1, please change "fluid is various embodiments" to read --fluid in various embodiments--.

Column 7, lines 37-38, please change "is provides" to read --is provided--.

Signed and Sealed this
Nineteenth Day of April, 2011

David J. Kappos
*Director of the United States Patent and Trademark Office*

Column 16, lines 9-12, please replace the sentence "It will be understood by those skilled in the art this type of detection and regulation may also be used with in conjunction with the other embodiments of the present invention described above." with --It will be understood by those skilled in the art that this type of detection and regulation may also be used in conjunction with other embodiments of the present invention described above.--.

Column 17, line 67, please change "scanning laser beam was the done by on-the-fly adjustments" to read --scanning laser beam was done by on-the-fly adjustments--.

IN CLAIM 6:

Column 20, line 20, please change "claim 1" to read --claim 1--.

IN CLAIM 17:

Column 21, line 15, please change "there into" to read --thereinto--.

IN CLAIM 22:

Column 22, lines 13-14, please cancel the text "and the secondary treatment device is a membrane".

IN CLAIM 24:

Column 22, line 43, please change "into the second extraction fluid" to read --into the extraction fluid--.

Column 22, line 48, please change "alone a membrane" to read --along a membrane--.